(12) United States Patent
Karsdon et al.

(10) Patent No.: US 11,819,684 B2
(45) Date of Patent: Nov. 21, 2023

(54) ELECTRICAL INHIBITION (EI) UTERINE PACEMAKER FOR CONTROLLING UTERINE CONTRACTIONS

(71) Applicant: NEW YORK UNIVERSITY, New York, NY (US)

(72) Inventors: Jeffrey Karsdon, New York, NY (US); Frederick Naftolin, New York, NY (US); Vikram Kapila, New York, NY (US); Ashwin Raj Kumar, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 39 days.

(21) Appl. No.: 17/712,625

(22) Filed: Apr. 4, 2022

(65) Prior Publication Data

US 2022/0288384 A1    Sep. 15, 2022

Related U.S. Application Data

(63) Continuation of application No. 16/470,312, filed as application No. PCT/US2017/067556 on Dec. 20, 2017, now Pat. No. 11,291,831.

(Continued)

(51) Int. Cl.
*A61N 1/05* (2006.01)
*A61N 1/08* (2006.01)
(Continued)

(52) U.S. Cl.
CPC ............ *A61N 1/0524* (2013.01); *A61N 1/08* (2013.01); *A61N 1/378* (2013.01); *A61N 1/37223* (2013.01); *A61N 1/37282* (2013.01)

(58) Field of Classification Search
CPC .... A61N 1/0524; A61N 1/08; A61N 1/37223; A61N 1/37282; A61N 1/378
See application file for complete search history.

(56) References Cited

U.S. PATENT DOCUMENTS

| 5,447,526 A | 9/1995 | Karsdon |
| 5,713,940 A * | 2/1998 | Karsdon ............ A61N 1/36031 |
| | | 607/39 |

(Continued)

FOREIGN PATENT DOCUMENTS

| WO | 2014035977 A1 | 3/2014 |
| WO | 2015058128 A1 | 4/2015 |

OTHER PUBLICATIONS

International Search Report dated Feb. 26, 2018 issued in PCT/US2017/067556.

*Primary Examiner* — Shirley X Jian
(74) *Attorney, Agent, or Firm* — SCULLY SCOTT MURPHY AND PRESSER

(57) ABSTRACT

In an aspect of the present disclosure, a system and method for controlling uterine contractions is disclosed including receiving data from at least one sensor by a wireless apparatus inserted into the patient's vagina adjacent the cervix. The data includes an indication that a contraction of the uterus is imminent. The method further includes in response to receiving the data, causing a generator circuit of the wireless apparatus to supply electrical energy to an energy applicator of the wireless apparatus that is configured to apply the supplied electrical energy to the uterus of the patient via the cervix of the patient to control contractions of the patient's uterus.

22 Claims, 16 Drawing Sheets

Related U.S. Application Data

(60) Provisional application No. 62/436,943, filed on Dec. 20, 2016.

(51) Int. Cl.
*A61N 1/372* (2006.01)
*A61N 1/378* (2006.01)

(56) References Cited

U.S. PATENT DOCUMENTS

| | | |
|---|---|---|
| 5,964,789 A | 10/1999 | Karsdon |
| 6,694,192 B2 | 2/2004 | Policker et al. |
| 8,606,371 B2 | 12/2013 | Garfield et al. |
| 8,874,183 B2 | 10/2014 | Aina-Mumuney et al. |
| 8,972,028 B2 | 3/2015 | Garfield et al. |
| 8,992,409 B2 | 3/2015 | Forsell |
| 9,731,120 B2 | 8/2017 | Garfield et al. |
| 9,872,983 B2 | 1/2018 | Garfield et al. |
| 10,039,472 B2 | 8/2018 | Aina-Mumuney et al. |
| 2002/0010494 A1 | 1/2002 | Policker et al. |
| 2013/0053670 A1 | 2/2013 | Aina-Mumuney et al. |
| 2013/0261702 A1 | 10/2013 | Garfield et al. |
| 2014/0065107 A1 | 3/2014 | Lockwood et al. |
| 2014/0180169 A1 | 6/2014 | Peters et al. |
| 2015/0216472 A1 | 8/2015 | Aina-Mumuney et al. |
| 2016/0331299 A1* | 11/2016 | Cline .................... A61B 5/721 |
| 2017/0035347 A1* | 2/2017 | Cantor ................ A61B 5/6875 |
| 2018/0317835 A1 | 11/2018 | Groberman et al. |
| 2020/0107771 A1 | 4/2020 | Penders et al. |
| 2020/0196958 A1 | 6/2020 | Penders et al. |
| 2020/0353247 A1 | 11/2020 | Ahn et al. |
| 2021/0016098 A1 | 1/2021 | Gei et al. |
| 2021/0161460 A1* | 6/2021 | Brown .................. A61B 5/435 |

* cited by examiner

ELECTRICAL INHIBITION (EI) UTERINE PACEMAKER FOR CONTROLLING UTERINE CONTRACTIONS

CROSS-REFERENCE TO RELATED APPLICATIONS

This application is a Continuation Application of U.S. Ser. No. 16/470,312 filed Jun. 17, 2019, which is a national phase application of International Patent Application No. PCT/US2017/067556 filed on Dec. 20, 2017, which claims benefit of priority to U.S. Provisional Application Ser. No. 62/436,943 filed Dec. 20, 2016, the entire contents of which each are incorporated herein by reference.

TECHNICAL FIELD

The present disclosure relates to the control of pre-term uterine contractions, and in particular to the use of an electrical inhibition (EI) uterine pacemaker.

BACKGROUND

Preterm birth prevention is a major unmet goal of neonatal/perinatal medicine. Preterm births are still a very important medical and public health problem and are associated with very high costs, monetary and non-monetary, to parents and society. The United States and Western Europe each have about a half a million preterm births per year. This constitutes national health care expenditures well over $26 billion and possibly as high as $50 billion. Preterm birth is the primary cause of morbidity and mortality among infants in the world. Costs resulting from a preterm birth increase with decreasing gestational age.

Preterm births have continued to increase despite the current standard of care and the availability of pharmaceuticals to stop uterine contractions, known as tocolytics. The prevalence of preterm birth has been rising steadily from about 9% in 1981 to 12.7% in 2005. Tocolytics, however, provide limited value other than delaying preterm birth due to preterm labor for 72 hours. In addition, the systemic nature of tocolytics often results in side effects necessitating discontinuation. Therefore, other modalities that could significantly delay or prevent spontaneous preterm birth are necessary.

BRIEF SUMMARY

The systems, methods, apparatus described herein provide ways to control pre-term uterine contractions.

In an aspect of the present disclosure, a wireless apparatus for controlling uterine contractions is disclosed. The wireless apparatus includes a housing configured for removable insertion into the vagina of a patient adjacent the uterine cervix and an energy generating device coupled to the housing. The energy generating device includes first and second electrodes that are configured to apply electrical energy to the cervix of the patient. The energy-generating device also includes a battery in electrical communication with the first and second electrodes and a wireless communication interface configured to wirelessly receive data from at least one external sensor. The data includes an indication that an electrical signal has been sensed by the at least one sensor from the uterus of the patient. The sensed electrical signal indicates that a contraction of the uterus is imminent. The energy generating device also includes a generator circuit in electrical communication with the first and second electrodes and the battery. The generator circuit is configured to cause the battery to supply electrical energy to the first and second electrodes. The first and second electrodes are configured to apply the electrical energy to the uterus of the patient via the approximation of the electrodes to the cervix of the patient, to control contractions of the uterus. The energy generating device also includes an impedance matching circuit in electrical communication with the first and second electrodes. The impedance matching circuit is configured to determine an impedance value of the cervix of the patient based on electrical energy applied to the cervix by the first and second electrodes. The energy generating device also includes a controller in electrical communication with the wireless communication interface, the generator circuit, and the impedance matching circuit. The controller is configured to receive the data from the at least one sensor via the wireless communication interface, in response receiving the data, cause the generator circuit to supply electrical energy to the first and second electrodes from the battery to stimulate the uterus of the patient, receive the determined impedance value from the impedance matching circuit, and adjust the electrical energy supplied by the generator circuit to the first and second electrodes based on the determined impedance value. In some aspects, the internal sensing and stimulation circuits may be over-ridden by an external, operator-driven signal transmitted from a computing device associated medical or other personnel. In some aspects, the internal stimulation circuits may be over-ridden in an emergency by a manual emergency power cut-off switch disposed on the wireless apparatus.

In an aspect, the energy generating device may further include at least a third electrode in electrical communication with the generator circuit. The generator circuit may be configured to cause the battery to supply electrical energy to the third electrode. The third electrode may be configured to apply the electrical energy to the cervix of the patient to stimulate the uterine cervix, and thereby stimulate the rest of the uterus of the patient as would be used for lack of uterine contractions post-partum. Lack of uterine contractions post-partum is the main cause of post-partum hemorrhage and maternal death. In some aspects, at least a 4th electrode (e.g., at least two pairs of electrodes) may be included where, for example, the second set of electrodes may be configured as back-up electrodes in case of a lead failure in the first set of electrodes. For example, any 2 pairs of the electrodes can be used for different pulse parameters to inhibit or stimulate contractions and for "quadruple redundancy" back-up in case of a lead failure.

In another aspect, the housing may be configured to transition between a first state (e.g., an expanded state or shape) and at least a second state (e.g., a compressed state or shape). The second state may be configured for insertion into the vagina of the patient. In an aspect, the housing is biased toward the first state and may be configured to return toward the first state after placement in the vagina. The first state is configured to hold the device in place within the vagina, for example, with the electrodes positioned abutting or in contact with the patient's cervix placed for inhibiting pre-term labor. In some aspects, the first state of the housing may be determined, for example, by the manufacture such that the outer edge of the larger dimension of the housing contains a coiled spring that allows the housing to accommodate to the two states described.

In yet another aspect, the generator circuit may be configured to cause the battery to supply electrical energy to the first and second electrodes according to a waveform. For example, in some aspects, the generator circuit may be configured to cause the battery to supply electrical energy to the first and second electrodes in a square waveform.

In some aspects, the controller may be configured to cause the generator circuit to supply the electrical energy to the first and second electrodes in a plurality of pulses. In an aspect, the controller may be further configured to reverse a polarity of the electrical energy for at least one of the plurality of pulses.

In another aspect, the controller may be further configured to receive monitoring data from the at least one sensor. The monitoring data may be generated by the at least one sensor based at least in part on a sensed effect of the application of the electrical energy to the patient's uterus via the cervix. The controller may be further configured to cause the generator circuit to adjust the supply of electrical energy to the first and second electrodes based on the monitoring data.

In some aspects, the controller may be further configured to determine that the received impedance value is below a pre-determined threshold value and in response to the determination that the received impedance value is below a pre-determined threshold value, cause the generator circuit to adjust the supply of electrical energy to the first and second electrodes. In some aspects, the adjustment to the supply of electrical energy may be configured to enhance the counter-current to forestall the imminent contraction of the uterus.

In yet another aspect, the controller may be further configured to determine that the received impedance value is below a pre-determined threshold value and in response to the determination that the received impedance value is below a pre-determined threshold value, transmit data including values that furnish indications of the state of ripeness of the cervix for labor to a wireless controller associated with a physician.

In an aspect, the housing may be configured to transition between a first state and at least a second state. The second state may be configured for insertion into the vagina of the patient. In some aspects, the housing is biased toward the first state.

In an aspect of the present disclosure, a method for controlling uterine contractions is disclosed. The method includes receiving, via a wireless communication interface of a wireless apparatus inserted into the patient's vagina adjacent the cervix, data from at least one sensor. The data includes an indication that an electrical signal has been sensed by the at least one sensor from the uterus of the patient. The sensed electrical signal indicating that a contraction of the uterus is imminent. The method further includes in response to receiving the data, causing, by a controller of the wireless apparatus, a generator circuit of the wireless apparatus to supply electrical energy from a battery of the wireless apparatus to an energy applicator of the wireless apparatus. The energy applicator of the wireless apparatus is configured to apply the supplied electrical energy to the uterus of the patient via the cervix of the patient to control contractions of the patient's uterus.

In aspects of the present disclosure apparatus, systems, methods, and computer program products in accordance with the above aspect may also be provided.

BRIEF DESCRIPTION OF THE DRAWINGS

The details of the present disclosure, both as to its structure and operation, can best be understood by referring to the accompanying drawings, in which like reference numbers and designations refer to like elements.

DETAILED DESCRIPTION

The present disclosure provides methods, systems, and apparatus to control preterm uterine contractions and preterm birth.

Figure 1A:
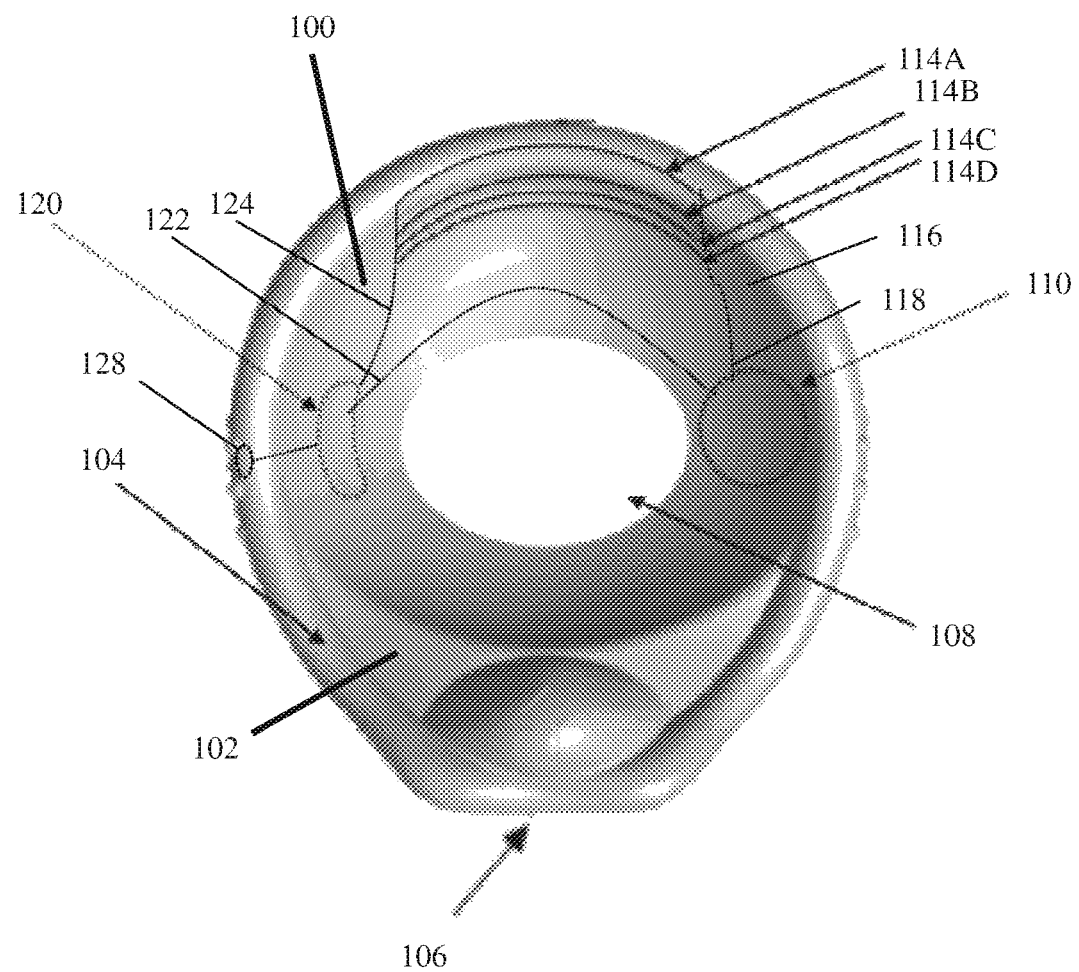
FIG. 1A is a top view illustrating an electrical inhibition (EI) uterine pacemaker in accordance with an aspect of the present disclosure.

With reference now to FIG. 1A, an electrical inhibition (EI) uterine pacemaker is illustrated. EI uterine pacemaker 100 includes a body or housing 102 that may be similar to, for example, a diaphragm, a pessary, or other similar structure that is configured for insertion into the vagina of a patient adjacent or proximate to the cervix of the patient. Body 102 may be formed, for example, of a biocompatible material that is suitable for insertion into the vagina of a patient. For example, body 102 may be formed of silicone, latex, or other similar biocompatible materials that are configured for long-term use in a human biological environment such as the vagina with minimal biological impact to surrounding tissue.

In some aspects, body 102 includes a rim 104 that is configured to transition between a collapsed state and an expanded state. For example, body 102 may be formed of a deformable material. Rim 104 may be transitioned toward the collapsed state by the patient, a doctor, a physician, or other medical personnel during insertion into the vagina of the patient and may be transitioned or allowed to expand toward the expanded state once positioned adjacent or proximate to the cervix of the patient to secure body 102 in position. Rim 104 may include or be formed of a shape memory material that is biased towards the expanded state. For example, in some aspects, rim 104 may include a biasing member 104A (FIG. 2), e.g., a coiled spring, nitinol memory wire, shape memory material or other biasing member that may bias rim 104 toward the expanded state. In some aspects, biasing member 104A may be covered or coated by a non-conductive membrane. In some aspects, for example, body 102 may be a diaphragm.

In some aspects, body 102 may be formed of a rigid material and may be inserted by the patient, doctor, physician, or other medical personnel as is without transitioning to a collapsed state. For example, body 102 may be a pessary. In some aspects, body 102 may include one or more perforations to facilitate the flow of fluids through the body 102.

In some aspects, body 102 may also include a relief arch 106 that may be manipulated by a doctor or the patient to remove the EI uterine device 100.

Figure 2:
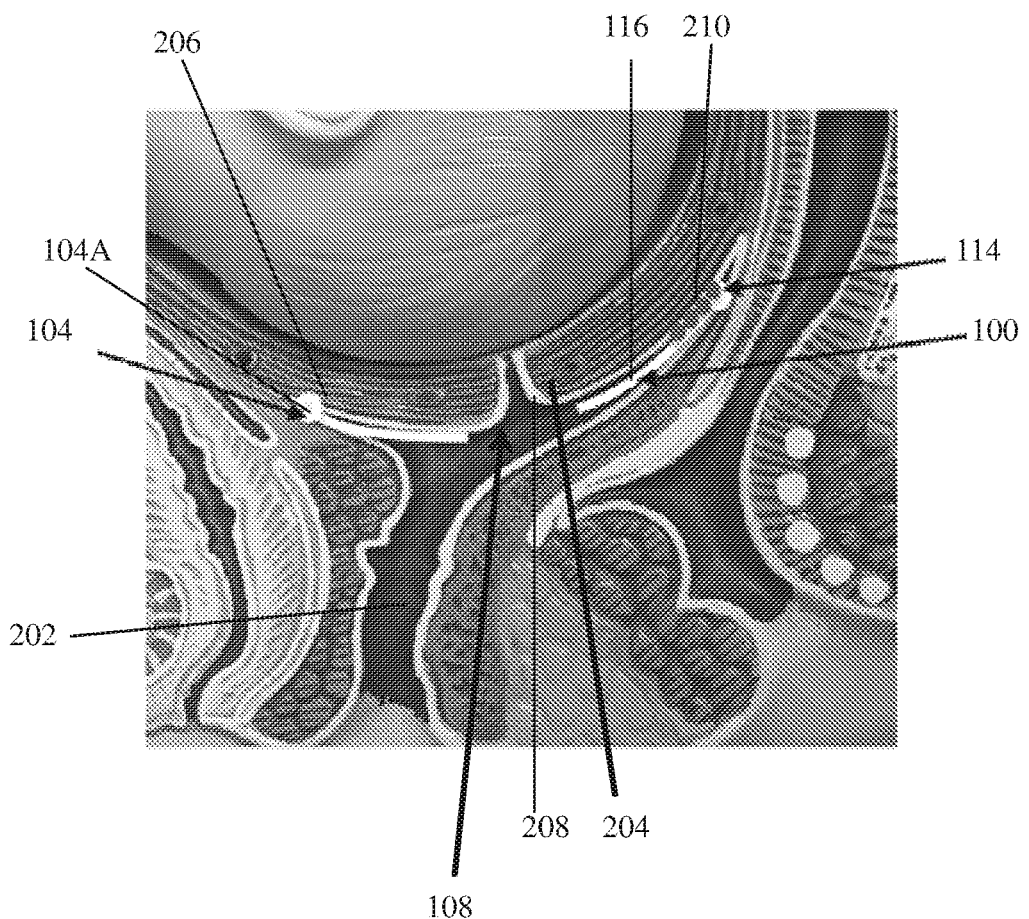
FIG. 2 is a diagram illustrating the insertion position of the EI uterine pacemaker of FIG. 1A or 1B in the vagina of a patient in accordance with an aspect of the present disclosure.

In some aspects, body 102 may also include an opening or through-hole 108. Opening 108 is configured such that when body 102 is positioned within the vagina of the patient adjacent or proximate to the cervix, for example, as illustrated in FIG. 2, opening 108 is positioned relative to the cervix such that fluids or other materials exiting the cervix may drain through opening 108.

With continued reference to FIG. 1A, EI uterine pacemaker 100 includes a power source 110 that is embedded or attached to body 102. For example, body 102 may be formed around power source 110 during production of body 102 or power source 110 may be subsequently attached to body 102 after body 102 has already been formed. Power source 110 may include, for example, a lithium-ion battery, Li/CFx battery or other similar power source. For example, a lithium-ion battery in the range of 3.7 volts and 2,000 milliampere-hours (mAh) may be used.

EI uterine pacemaker 100 also includes electrodes 114, for example, electrodes 114A, 114B, 114C, and 114D. In some aspects, EI uterine pacemaker 100 may include two electrodes, 114A and 114B. In some aspects, EI uterine pacemaker 100 may include three electrodes 114A, 114B, and 114C. In some aspects EI uterine pacemaker 100 may include four electrodes 114A, 114B, 114C, and 144D or even more electrodes 114. Electrodes 114 are positioned or disposed on a distal surface 116 of body 102 such that when EI uterine pacemaker 100 is inserted into the vagina of the patient and positioned adjacent to or proximate the cervix of the patient, distal surface 116 and electrodes 114 will be positioned towards the cervix and electrodes 114 may contact or abut an outer wall of the cervix, as further illustrated, for example, in FIG. 2.

In some aspects, electrodes 114 may be electrically connected to power source 110, for example, via electrical connections 118. For example, electrical connections 118 may be at least one, two or several wires. In some aspects, electrical connections 118 may be disposed on or embedded within body 102 and may, for example, be coated with a non-conductive membrane. In some aspects, electrical connections 118 may be a bundle of wires separately connecting each of electrodes 114A-114D to power source 110.

EI uterine pacemaker 100 also includes a receiver/controller 120. Receiver/controller 120 is configured to control the output of power source 110 to electrodes 114. For example, receiver/controller 120 may be electrically connected to power source 110, for example, via electrical connections 122. In some aspects, receiver/controller 120 may be electrically connected to electrodes 114 via power source 110 and may receive electrical feedback from electrodes 114 via power source 110. In some aspects, receiver/controller 120 may be directly connected to electrodes 114, for example, via electrical connections 124, and may receive electrical feedback directly from electrodes 114. In some aspects, for example, electrical connections 124 may be similar to electrical connections 118. In some aspects, each electrode 114 may have a separate electrical connection 124 to receiver/controller 120.

Figure 1B:
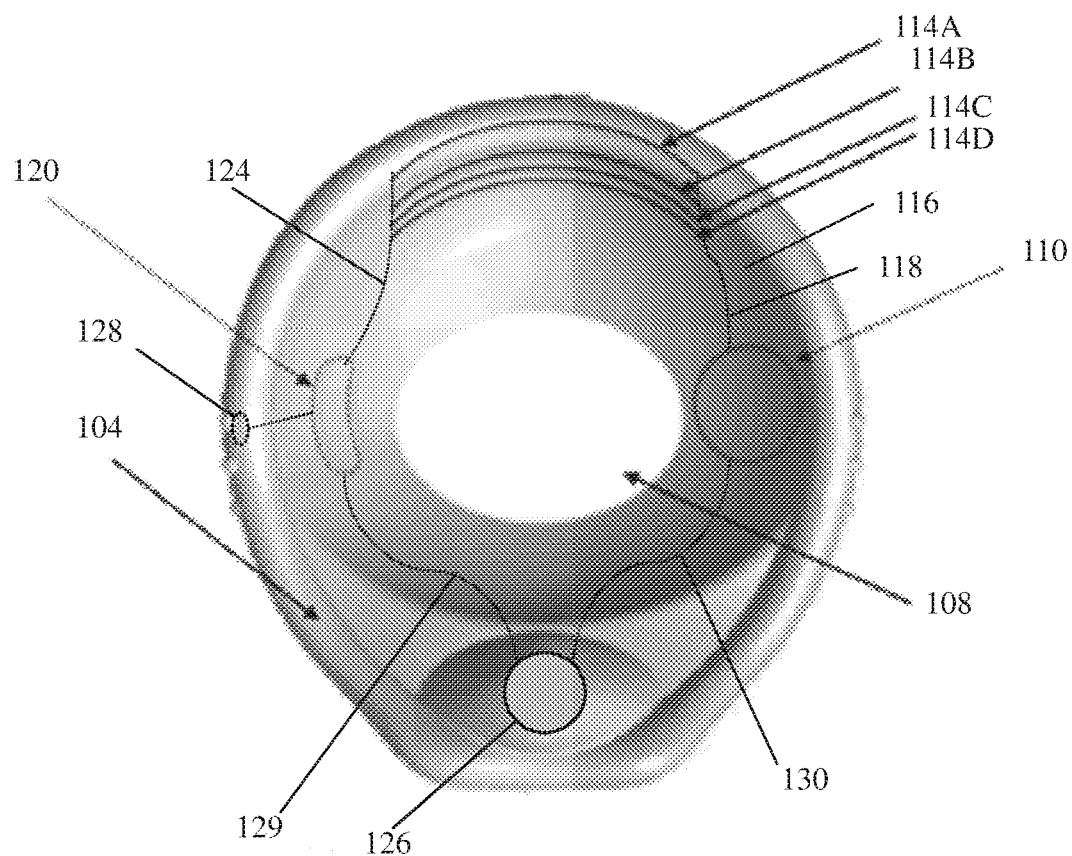
FIG. 1B is a top view illustrating an electrical inhibition (EI) uterine pacemaker in accordance with an aspect of the present disclosure.

In some aspects, with reference now to FIG. 1B, a manually operated master/emergency on/off switch 126 may be electrically disposed between power source 110 and receiver/controller 120 and may be actuated to disconnect or interrupt power between power source 110 and receiver/controller 120. For example, switch 126 may be connected to receiver/controller 120 via an electrical connection 129 and may be separately connected to power source 110 via an electrical connection 130. If a physician, user, patient or other medical personnel wishes to manually shut off EI uterine pacemaker 100, master/emergency on/off switch 126 may be actuated or depressed between an activated position and a deactivated position to control the flow of energy between the power source 110 and receiver/controller 120, and therefore to electrodes 114A-D. In some aspects, for example, to prevent inadvertent shut-off of EI uterine pacemaker 100, switch 126 may be required to be held by the user for a pre-determined period of time before EI uterine pacemaker is shut off, e.g., 5-10 seconds, or any other predetermined period of time. In some aspects, for example, switch 126 may include a tactile surface that feels different than the rest of EI uterine pacemaker 100 to facilitate easy identification of the location of switch 126 by a physician or other user without requiring visual confirmation. In some aspects, for example, master/emergency on/off switch 126 may include or be illuminated by, for example, LED's or other similar illumination sources, such that the status of switch 126 may be visually confirmed. For example, when EI uterine pacemaker 100 is active, e.g., switch 126 is in the activated position and allows current to flow, switch 126 or an LED may illuminate in a first color, e.g., green, while when EI uterine pacemaker 100 is deactivated, e.g., switch 126 is in the deactivated position and interrupts current flow, switch 126 or an LED may be illuminated in a second color, e.g., red.

In some aspects, referring again to FIGS. 1A and 1B, EI uterine pacemaker 100 may include a socket 128 that is configured to receive an electrical connection. Socket 128 is electrically connected to receiver/controller 120 and is configured to provide a direct connection to receiver/controller 120. For example, in the event that the wireless connection is not functioning properly (e.g., an emergency situation), EI uterine pacemaker 100 may be controller through a direct wired connection via socket 128. For example, a plug or wire may be inserted into socket 128 and may extend out of the patient's vagina for direct connection to wireless controller 706 such that wireless controller 706 may control the function of EI uterine pacemaker 100 via a direct non-wireless connection if needed.

The function of receiver/controller 120 will be described in more detail below with reference to FIGS. 3-6.

Referring now to FIG. 2, an example insertion position for EI uterine pacemaker 100 is illustrated. During insertion, body 102 of EI uterine pacemaker 100 may be transitioned to a collapsed state and body 102 may be inserted into the patient's vagina 202 until the body 102 is positioned adjacent or proximate to the patient's cervix 204. Once in position, the body 102 may be allowed to transition back toward the expanded state due to the bias of rim 104. As the body 102 is transitioned toward the expanded state, rim 104 is positioned adjacent or proximate to an outer portion 206 of cervix 204 and in some aspects may be biased against outer portion 206 of cervix 204 to maintain a position of body 102 adjacent or proximate to cervix 204. In some aspects, for example, rim 104 may abut or contact outer portion 206.

When body 102 is in position adjacent or proximate to cervix 204, opening 108 of body 102 is positioned adjacent or proximate to the external os 208 of the cervix 204 such that any fluids or other biological materials exiting cervix 204 may travel through opening 108.

When body 102 is in position adjacent or proximate to cervix 204, electrodes 114 disposed on distal surface 116 of body 102 are positioned adjacent or proximate to and preferably abutting or in contact with an outer portion or wall 210 of cervix 204 as illustrated in FIG. 2. In this configuration, the electrical energy supplied to electrodes 114 by power source 110 may be applied to outer portion 210 of cervix 204 such that the electrical energy applied to the cervix by electrodes 114 may affect the smooth muscle of the uterus to control uterine contractions.

FIGS. 3-6 illustrate example configurations that may implement EI uterine pacemaker 100.

Figure 3:
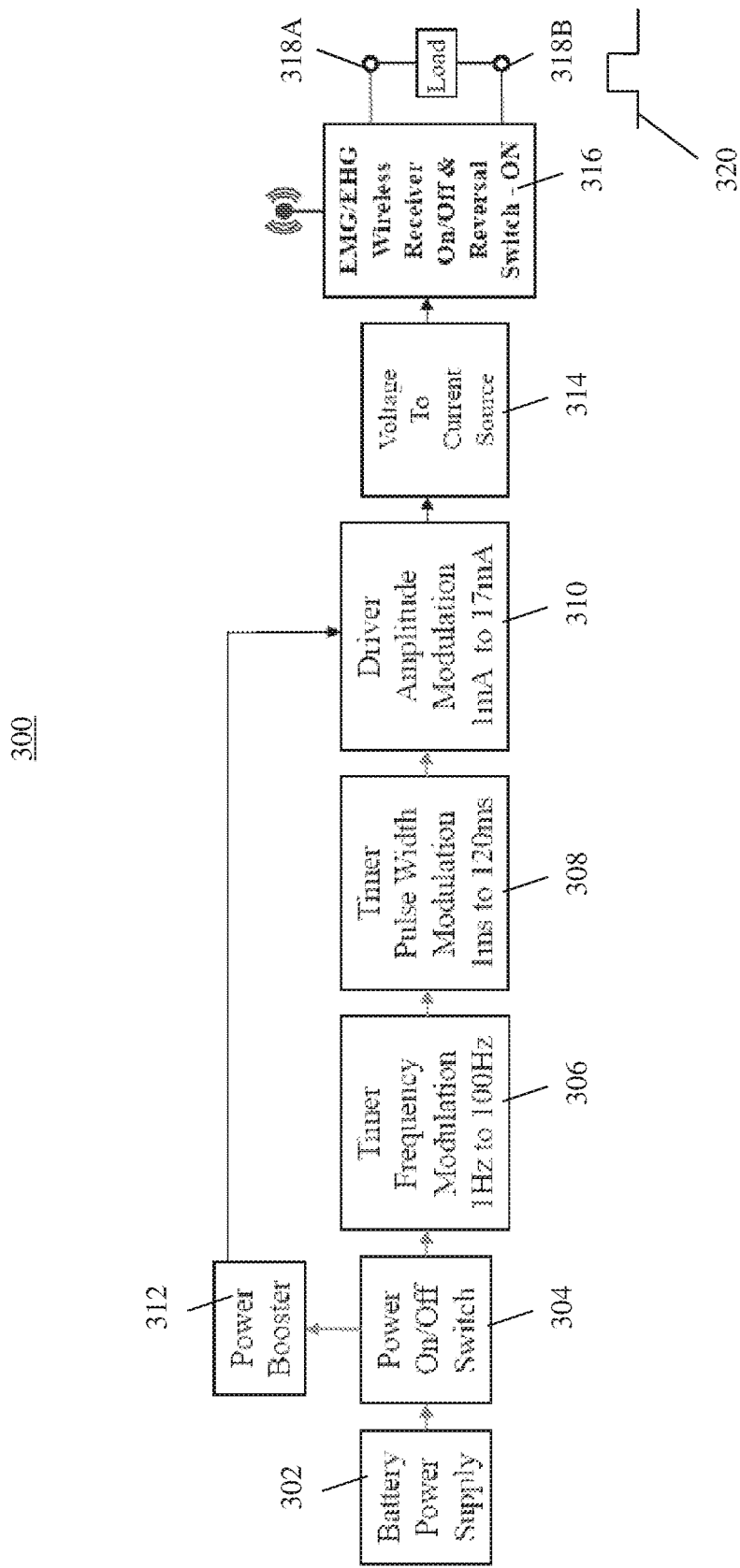
FIG. 3 is a system diagram illustrating a configuration of the EI uterine pacemaker of FIG. 1A or 1B having single pacing capability, bi-polar monophasic output, and electrode reversal in accordance with an aspect of the present disclosure.

With reference now to FIG. 3, a configuration 300 of EI uterine pacemaker 100 is disclosed that provides single pacing capability using a monophasic bi-polar output with electrode reversal.

Configuration 300 includes a power supply 302, for example a battery or other power source, a power on/off switch 304, a timer frequency modulator 306, a timer pulse width modulator 308, a driver amplitude modulator 310, a power booster 312, a voltage to current source 314, wireless receiver 316, and electrodes 318A and 318B. In configuration 300, for example, electrodes 318A and 318B may be implemented by any pair of electrodes 114A-114D. In some aspects, for example, EI uterine pacemaker 100 may only include a pair of electrodes, e.g., just 114A and 114B, when implemented by configuration 300. In some aspects, EI uterine pacemaker 100 may include all of electrodes 114A-114D when implemented by configuration 300 with a pair of electrodes, e.g., electrodes 114A and 114B, configured as active electrodes, and the remaining electrodes, e.g., electrodes 114C and 114D, configured as inactive electrodes. For example, the inactive electrodes may be used as spare electrodes in the event that one of the active electrodes is not functioning properly or loses contact with the cervical tissue. Any other pairs of electrodes may be active or inactive.

Power on/off switch 304 may, for example, be a physical switch (e.g., switch 126 of FIG. 1) found on body 102. For example, when EI uterine pacemaker 100 is packaged for shipping by a manufacturer, power on/off switch 304 may be set to an "off" state, e.g., power supply 302 may be isolated from timer frequency modulator 306 and power booster 312. When the physician or other medical personnel removes the EI uterine pacemaker 100 from the packaging, the physician or other medical personnel may switch power switch 304 to an "on" state such that power from power supply 302 is supplied to timer frequency modulator 306 and power booster 312 and EI uterine pacemaker 100 is ready for use. In some aspects, removal of the EI uterine pacemaker 100 from the shipping packaging by a physician or other medical personnel may automatically switch power switch 304 to the "on" state.

Timer frequency modulator 306 is configured to modulate the frequency of the electrical energy output by power supply 302 between 1 Hz and 100 Hz. For example, in some aspects, the frequency of the electrical energy may be modulated to a frequency in the range of about 10 Hz-20 Hz. In some aspects, the frequency may be modulated to control a depth of penetration of the electrical energy. For example, to affect the uterus, the electrical energy must first penetrate through the cervix. The frequency may be modulated by timer frequency modulator 306 to a level that penetrates to a desired level of tissue.

Timer pulse width modulator 308 is configured to modulate a pulse width of the frequency modulated electrical energy output by timer frequency modulator 306 using pulse width modulation to generate a monophasic waveform 320 for the electrical energy. For example, timer pulse modulator 308 may be configured to generate a sine waveform, a square waveform, a rectangular waveform, a triangular waveform, a saw-toothed waveform, a monophasic waveform, a biphasic waveform, a charge balanced waveform, a charge imbalanced waveform, or any other waveform having the modulated pulse width. Different pulse widths of the waveform 320 may influence the reaction of the target tissue in different ways. For example, shorter pulse widths may affect the nerves of the tissue while longer pulse widths may affect the muscles. In some aspects, for example, a waveform 320 having a pulse width that is equal to or less than 50% of the duty cycle, e.g., 50% of the time the current is applied to the target tissue to affect tissue function and 50% of the time the current is not applied or is applied at a low level that does not affect tissue function, may control muscle activity, while a waveform 320 having a pulse width that is shorter, e.g., 10% of the duty cycle may control nerve activity. The pulse width may be modulated by timer pulse width modulator 308 to control the desired portion of tissue.

Driver amplitude modulator 310 is configured to modulate the amplitude of the waveform output by timer pulse width modulator 308 between 1 mA and 20 mA. For example, in some aspects, the waveform of electrical energy may be modulated to an amplitude in the range of about 5 mA to 17 mA and in some aspects to an average of 10 mA.

In some aspects, the power of the waveform to be modulated by driver amplitude modulator 310 may be boosted by power booster 312. Power booster 312 is configured to step up the voltage from the power source to a level needed to keep the output current constant at the varying tissue resistances/loads. For example, power booster 312 may step up voltage from the power source from 3.7 volts to 30 volts. In some aspects, for example, in order to maintain a constant current output while the tissue resistance/load changes during the progression of labor, a voltage of about 30 volts may be used before saturation occurs and the current drops.

Voltage to current source 314 produces a constant output current based on the amplitude modulated waveform output by driver amplitude modulator 310. Applying constant current is an efficient way of controlling muscle activity where, for example, the muscle activity depends on the ion (calcium, potassium etc.) current flows through membrane channels. The constant output current produced by the voltage to current source 314 may be applied efficiently even in the presence of a tissue having varying tissue resistance.

Wireless receiver 316 is configured to wirelessly transmit and receive data and to control the function of EI uterine pacemaker 100. For example, wireless receiver 316 may receive data from a wireless controller 706 (FIG. 7), for example, a device used by a physician to configure any of timer frequency modulator 306, timer pulse width modulator 308, driver amplitude modulator 310, power booster 312, and voltage to current source 314, to control the electrical energy output at electrodes 318A and 318B. In some aspects, wireless receiver 316 may be configured as an on/off switch similar to power on/off switch 304 where, for example, EI uterine pacemaker 100 may be turned on and off remotely by wireless controller 706. In some aspects, for example, if the wireless controller 706 is unable to communicate with the EI uterine pacemaker 100, a signal may also or alternatively be transmitted from sensor 702 to turn off EI uterine pacemaker 100. For example, sensor 702 may be used as a backup system for wireless controller 706 for the purpose of turning off EI uterine pacemaker 100.

In some aspects, wireless receiver 316 may be configured to reverse a polarity of the electrical energy output at electrodes 318A and 318B. For example, in some aspects, electrode 318A may initially be configured as the positive electrode while electrode 318B may initially be configured as the negative electrode. Wireless receiver 316 may reverse the polarity of the electrodes 318A, 318B such that electrode 318A is the negative electrode and electrode 318B is the positive electrode. Wireless receiver 316 may, for example, reverse the polarity in response to the receipt of a signal or command from wireless controller 706. Reversing the polarity of the electrodes provides a benefit because muscle response to an electrical current at the positive pole (anode) is different from the response at the negative pole (cathode). Accordingly, the level of effect or benefit from the application of electrical energy to the muscles of the cervix and uterus may depend on the direct of current flow.

Electrodes 318A and 318B are electrical contacts that are configured to transmit electrical energy to a target tissue location, e.g., wall 210 of cervix 204. In some aspects, electrodes 318A and 318B are configured to contact the target tissue location and transmit electrical energy through tissue at the target tissue location. The transmission of electrical energy through the tissue may stimulate the target tissue location and in some aspects tissue locations adjacent or proximate to the target tissue location or otherwise in electrical communication with the target tissue location. For example, the application of electrical energy to the wall 210 of cervix 204 may stimulate the smooth muscles of the uterus. This allows the smooth muscle of the uterus to be controlled, e.g., to reduce or eliminate a contraction, induce a contraction, or other similar forms of control.

Figure 4:
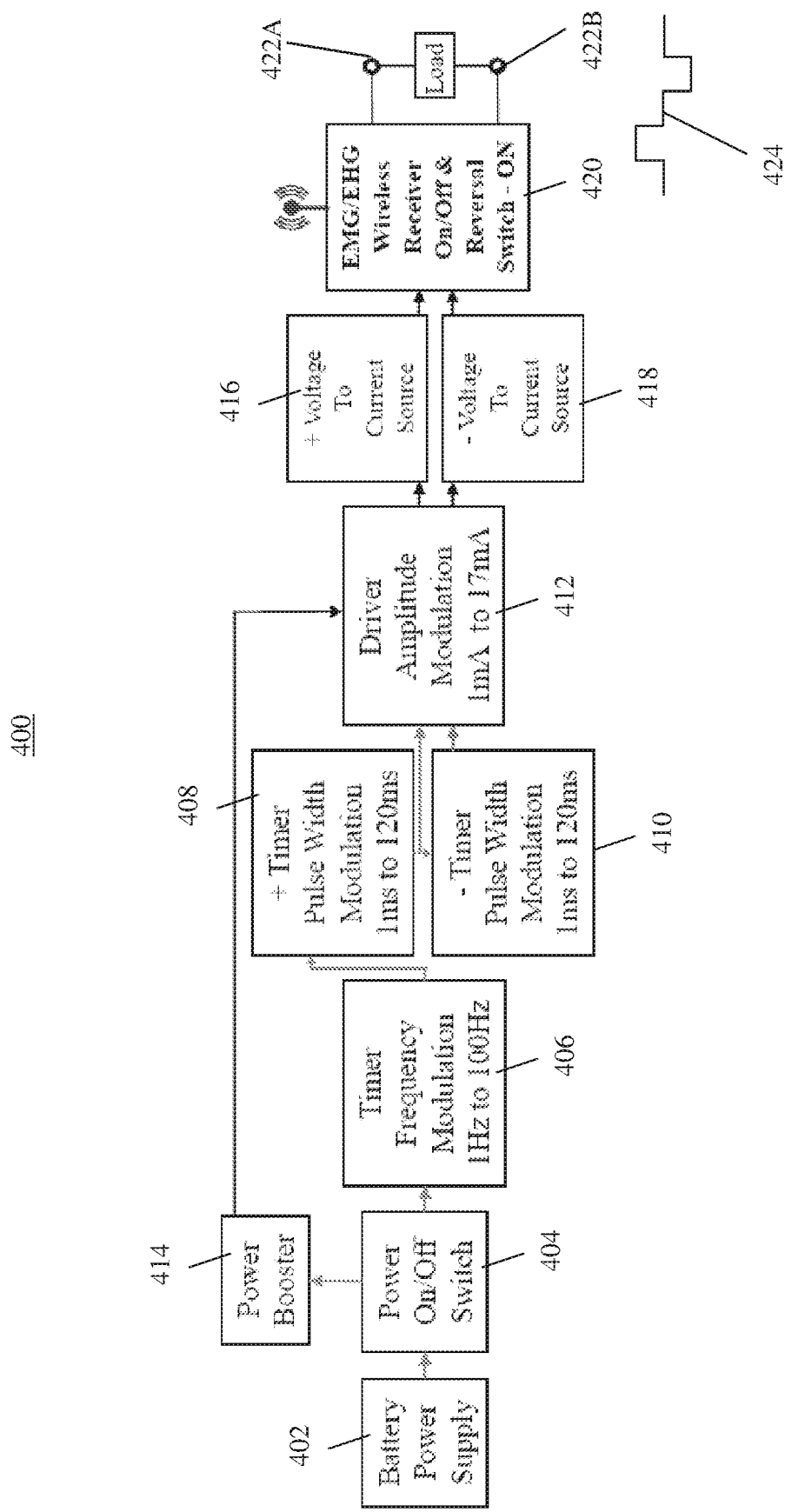
FIG. 4 is a system diagram illustrating another configuration of the EI uterine pacemaker of FIG. 1A or 1B having single pacing capability, bi-polar biphasic output, and electrode reversal in accordance with an aspect of the present disclosure.

With reference now to FIG. 4, a configuration 400 of EI uterine pacemaker 100 is disclosed that provides single pacing capability using a biphasic bi-polar output with electrode reversal.

Configuration 400 includes a power supply 402 similar to power supply 302. Power supply 402 supplies electrical energy to a power on/off switch 404 that function similarly to power on/off switch 304. The electrical energy output from power on/off switch 404 is then frequency modulated by a timer frequency modulator 406 that functions similar to timer frequency modulator 306. The electrical energy output from power on/off switch 404 is also power boosted by a power booster 414 that functions similar to power booster 312.

The frequency modulated electrical energy output from timer frequency modulator 406 is fed into a positive polarity timer pulse width modulator 408 which generates a biphasic energy waveform 424 using pulse-width modulation in a similar manner to timer pulse width modulator 308. The generated energy waveform 424 is fed into a negative polarity timer pulse width modulator 410 to further modulate the waveform. The bi-phasic energy waveforms 424 generated from positive polarity timer pulse width modulator 408 and negative polarity timer pulse width modulator 410 are also fed into a driver amplitude modulators 412 which modulates the amplitude of the waveforms 424 in a similar manner to driver amplitude modulator 310 of configuration 300. The amplitude modulation may also be power boosted by the output of power booster 414. The negative and positive polarity timer pulse width modulators 408 and 410 may be used to minimize the buildup of charged particles on the electrodes.

The amplitude modulated waveform 424 of the positive polarity timer pulse width modulator 408 is fed into a positive voltage to current sources 416 and the amplitude modulated waveform 424 of the negative polarity timer pulse width modulator 410 is fed into a negative voltage to current source 418 to produce respective output currents.

The output currents are controlled by a wireless receiver 420 that is configured similarly to wireless receiver 316 to wirelessly transmit and receive data and to control the function of EI uterine pacemaker 100 as described above with respect to configuration 300. For example, wireless receiver 420 may receive data from a wireless controller 706 (FIG. 7) to configure any of timer frequency modulator 406, positive polarity timer pulse width modulator 408, negative polarity timer pulse width modulator 410, driver amplitude modulator 412, power booster 414, and positive and negative voltage to current sources 416 and 418 to control the output of electrical energy to paired electrodes 422A and 422B. In addition, wireless receiver 420 may be configured to select or alternate the output of electrical energy to the electrodes 422A and 422B between the output waveforms 424 of positive polarity voltage to current source 416 and negative polarity voltage to current source 418.

In configuration 400, electrodes 422A and 422B may be implemented by any pair of electrodes 114A-114D. In some aspects, for example, EI uterine pacemaker 100 may only include a pair of electrodes, e.g., just 114A and 114B, when implemented by configuration 400. In some aspects, EI uterine pacemaker 100 may include all of electrodes 114A-114D when implemented by configuration 400 with a pair of electrodes, e.g., electrodes 114A and 114B, configured as active electrodes, and the remaining electrodes, e.g., electrodes 114C and 114D, configured as inactive electrodes. Any other pairs of electrodes may be active or inactive.

Figure 5:
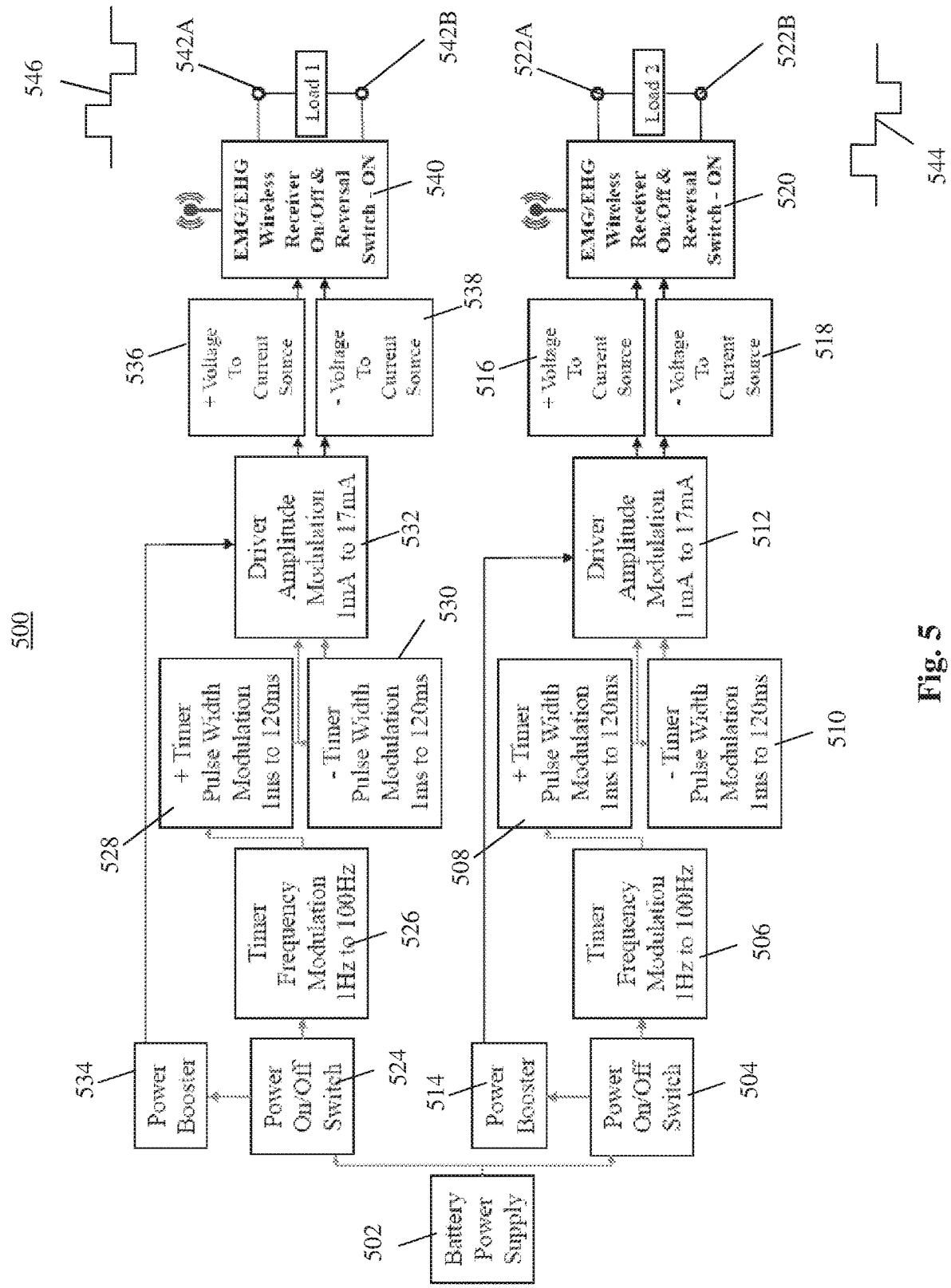
FIG. 5 is a system diagram illustrating yet another configuration of the EI uterine pacemaker of FIG. 1A or 1B having double pacing capability, bi-polar biphasic output, and electrode reversal in accordance with an aspect of the present disclosure.

With reference now to FIG. 5, a configuration 500 of EI uterine pacemaker 100 is disclosed that provides dual pacing capability using a biphasic output with electrode reversal.

Configuration 500 includes a power supply 502 similar to power supply 302. Power supply 502 supplies electrical energy to a pair of a power on/off switches 504 and 524 that function similarly to power on/off switch 304. The electrical energy output from each of power on/off switches 504, 524 is then frequency modulated by respective timer frequency modulators 506 and 526 that function similar to timer frequency modulator 306. The electrical energy output from each power on/off switch is also power boosted by respective power boosters 514 and 534 that function similar to power booster 312. In some aspects, for example, a single power on/off switch may implement both of switches 504 and 524 and control the power is supplied both timer frequency modulators 506 and 526 at the same time.

The frequency modulated electrical energy outputs from timer frequency modulators 506 and 526 are fed into respective positive polarity timer pulse width modulators 508 and 528 which generate biphasic energy waveforms 544, 546 using pulse-width modulation in a similar manner to timer pulse width modulator 308. The generated energy waveforms 544, 546 are fed into respective negative polarity timer pulse width modulators 510 and 530 to further modulate the waveform 544, 546 in a similar manner to negative polarity timer pulse width modulator 410. The energy waveforms 544, 546 generated from positive polarity timer pulse width modulators 508, 528 and negative polarity timer pulse width modulators 510, 530 are also fed into respective driver amplitude modulators 512, 532 which modulate the amplitude of the waveforms 544, 546 in a similar manner to driver amplitude modulator 310 of configuration 300. The amplitude modulation may also be power boosted by the output of power boosters 514 and 534.

The amplitude modulated waveforms 544, 546 of the positive polarity timer pulse width modulators 508 and 528 are fed into respective positive voltage to current sources 516, 536 and the amplitude modulated waveforms 544, 546 of the negative polarity timer pulse width modulators 510 and 530 are fed into respective negative voltage to current sources 518, 538 to produce respective output currents.

The output currents are controlled by respective wireless receivers 520, 540 that are configured similarly to wireless receiver 316 to wirelessly transmit and receive data and to control the function of EI uterine pacemaker 100 as described above with respect to configuration 300. For example, wireless receivers 520 and 540 may receive data from a wireless controller 706 (FIG. 7) to configure any of timer frequency modulators 506, 526, positive polarity timer pulse width modulators 508, 528, negative polarity timer pulse width modulators 510, 530, driver amplitude modulators 512, 532, power boosters 514, 534, and positive and negative voltage to current sources 516, 536 and 518, 538 to control the output of electrical energy to paired electrodes 522A and 522B, and paired electrodes 542A and 542B. In addition, wireless receiver 520 may be configured to select or alternate the output of electrical energy to the electrodes 522A and 522B between the output waveforms of positive polarity voltage to current source 516 and negative polarity voltage to current source 518. Likewise, wireless receiver 540 may be configured to select or alternate the output of electrical energy to the electrodes 542A and 542B between the output waveforms 544, 546 of positive polarity voltage to current source 536 and negative polarity voltage to current source 538. In some aspects, wireless controller 706 may be configured to control the output of electrical energy to each of electrodes 522A, 522B, 542A, and 542B as needed to provide dual pacing control of the uterus of the patient.

In configuration 500, electrodes 522A and 522B may be implemented by any pair of electrodes 114A-114D. Likewise, electrodes 542A and 542B may be implemented by any pair of electrodes 114A-114D.

Figure 6:
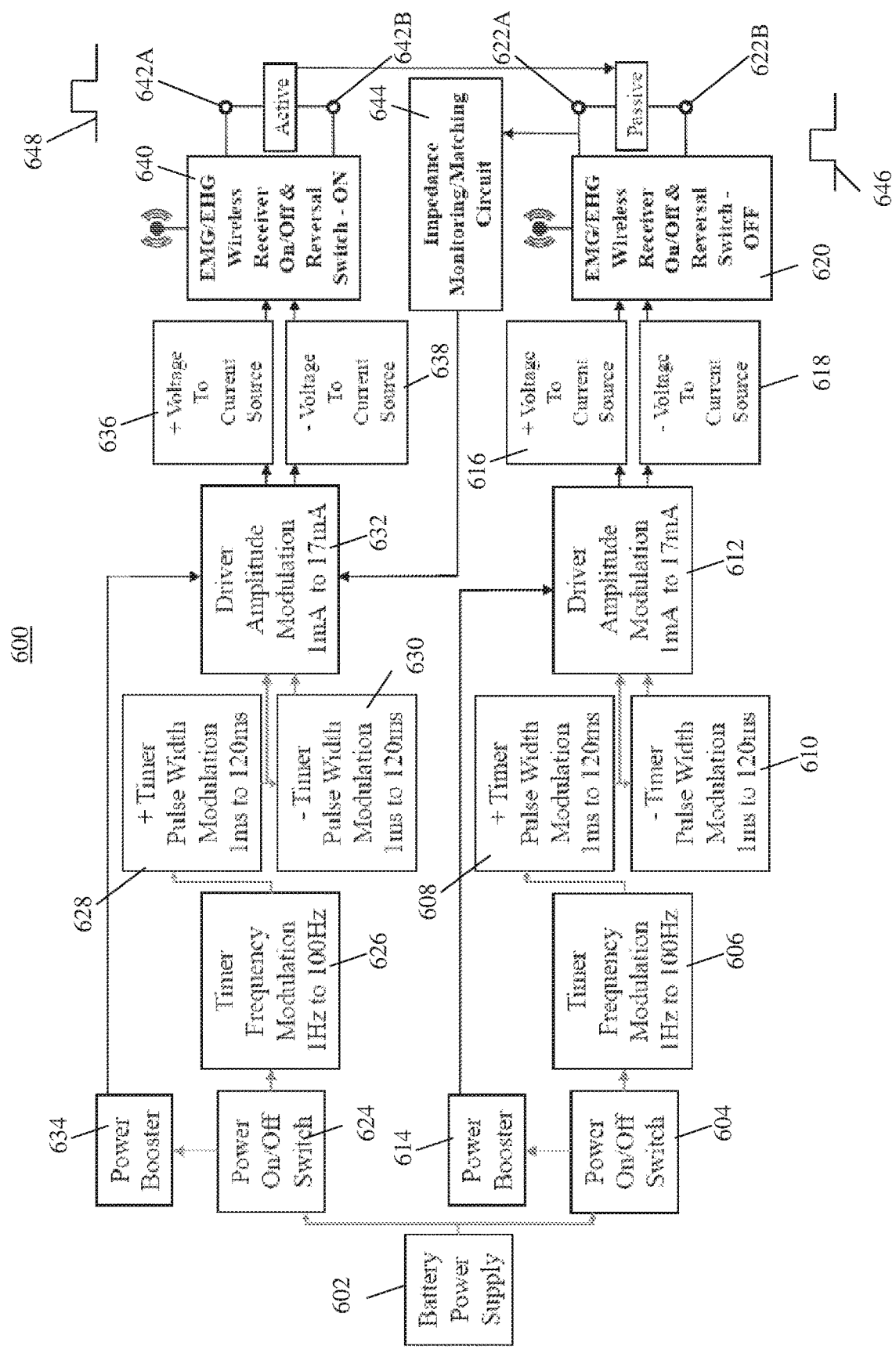
FIG. 6 is a system diagram illustrating another configuration of the EI uterine pacemaker of FIG. 1A or 1B having double pacing capability, bi-polar biphasic output, electrode reversal and an impedance monitoring and matching circuit in accordance with an aspect of the present disclosure.

With reference now to FIG. 6, a configuration 600 of EI uterine pacemaker 100 is disclosed that provides dual pacing capability using a biphasic bi-polar output with electrode reversal and impedance monitoring and matching. Configuration 600 is similar to configuration 500 with the addition of an impedance monitoring and matching circuit 644.

For example, configuration 600 includes a power supply 602 similar to power supply 502. Power supply 602 supplies electrical energy to a pair of a power on/off switches 604 and 624 that function similarly to power on/off switches 504 and 524. The electrical energy output from each of power on/off switches 604, 624 is then frequency modulated by respective timer frequency modulators 606 and 626 that function similar to timer frequency modulators 506 and 526. The electrical energy output from each power on/off switch is also power boosted by respective power boosters 614 and 634 that function similar to power boosters 514 and 534. In some aspects, for example, a single power on/off switch may implement both of 604 and 624 and control the power is supplied both timer frequency modulators 606 and 626 at the same time.

The frequency modulated electrical energy outputs from timer frequency modulators 606 and 626 are fed into respective positive polarity timer pulse width modulators 608 and 628 which generate biphasic energy waveforms 646, 648 using pulse-width modulation in a similar manner to positive polarity timer pulse width modulators 508 and 528. The generated energy waveforms 646, 648 are fed into respective negative polarity timer pulse width modulators 610 and 630 to further modulate the waveform 646, 648 in a similar manner to negative polarity timer pulse width modulators 510 and 530. The energy waveforms 646, 648 generated from positive polarity timer pulse width modulators 608, 628 and negative polarity timer pulse width modulators 610, 630 are also fed into respective driver amplitude modulators 612, 632 which modulate the amplitude of the waveforms in a similar manner to driver amplitude modulators 512 and 532 of configuration 500. The amplitude modulation may also be power boosted by the output of power boosters 614 and 634.

The amplitude modulated waveforms 646, 648 of the positive polarity timer pulse width modulators 608 and 628 are fed into respective positive voltage to current sources 616, 636 and the amplitude modulated waveforms 646, 648 of the negative polarity timer pulse width modulators 610 and 630 are fed into respective negative voltage to current sources 618, 638 to produce respective output currents.

The output currents are controlled by respective wireless receivers 620, 640 that are configured similarly to wireless receivers 520 and 540 to wirelessly transmit and receive data and to control the function of EI uterine pacemaker 100 as described above with respect to configuration 500. For example, wireless receivers 620 and 640 may receive data from a wireless controller 706 (FIG. 7) to configure any of timer frequency modulators 606, 626, positive polarity timer pulse width modulators 608, 628, negative polarity timer pulse width modulators 610, 630, driver amplitude modulators 612, 632, power boosters 614, 634, and positive and negative voltage to current sources 616, 636 and 618, 638 to control the output of electrical energy to paired electrodes 622A and 622B, and paired electrodes 642A and 642B. In addition, wireless receiver 620 may be configured to select or alternate the output of electrical energy to the electrodes 622A and 622B between the output waveforms of positive polarity voltage to current source 616 and negative polarity voltage to current source 618. Likewise, wireless receiver 640 may be configured to select or alternate the output of electrical energy to the electrodes 642A and 642B between the output waveforms of positive polarity voltage to current source 636 and negative polarity voltage to current source 638. In some aspects, wireless controller 706 may be configured to control the output of electrical energy to each of electrodes 622A, 622B, 642A, and 642B as needed to provide dual pacing control of the uterus of the patient.

In configuration 600, electrodes 622A and 622B may be implemented by any pair of electrodes 114A-114D. Likewise, electrodes 642A and 642B may be implemented by any pair of electrodes 114A-114D.

Configuration 600 further includes impedance monitoring and matching (IMM) circuit 644. IMM circuit 644 monitors the electrical impedance of any tissue in contact with any of electrodes 622A, 622B, 642A, and 642B to determine a state of the tissue. For example, one or more of electrodes 622A, 622B, 642A, and 642B may maintain output of a low level electrical current through the tissue and may measure an impedance of the tissue based on the current. For example, in some aspects, the low level electrical current may be in the range of about 10 μA to 10 mA. In some aspects, for example, electrodes 622A and 622B may be implemented as passive electrodes that are configured to maintain the application of low level electrical current to the tissue and IMM circuit 644 may monitor the impedance of the tissue across electrode 622A and 622B. The measured impedance may be fed into driver amplitude modulator 632 to further adjust the amplitude of the electrical energy that will be output by electrodes 642A and 642B. In this manner, IMM circuit 644 provides a feed-back loop to the active electrodes 642A and 642B based on the impedance measured by passive electrodes 622A and 622B. In some embodiments any other combination of electrodes may be used by IMM circuit 644 to measure impedance. For example, one or both of active electrodes 642A and 642B may be used to output the low level electrical current in addition to outputting electrical energy to control the patient's uterus.

Although configurations 300-600 are each described with respect to a monophasic or biphasic output waveform, any of configurations 300-600 may be configured to output either of the monophasic and biphasic waveforms.

In some aspects, the measured impedance may be used as an indirect measure of tissue hydration. For example, in some aspects, the impedance value for tissue may range from about 2 to about 65 ohm·meter (Ω·m) depending on gestational age and stage of labor. For example, as the cervix prepares for labor, the cervix typically becomes more hydrated or "ripe" and impedance decreases. The measured impedance may depend on a variety of factors including, for example, electrode diameter, inter-electrode distance, electrode pressure on the tissue and frequency used to measure the impedance. An algorithm may be applied to the measured impedance to determine the "cervical ripeness", e.g., amount of hydration. For example, the impedance of the cervix may be initially measured to determine a baseline impedance. The impedance of the cervix may then be monitored to determine how much the impedance of the cervix has decreased relative to the baseline. The amount of decrease may indicate how much the cervix has progressed. In some aspects, the measured impedance may be compared to a predetermined threshold impedance value to determine whether the cervix is "ripe". The pre-determine threshold impedance may be set, for example, by wireless controller 706 based on the gestational age of the baby and the stage of labor.

In some aspects, the determined cervical ripeness may be used to evaluate the likelihood of effacement and labor, for example, determine whether a contraction is an actual part of labor or a false alarm. For example, a physician may be able to use the output of the algorithm to determine what labor inhibiting treatments to employ and may use the output to determine the effectiveness of the labor inhibiting treatments.

In some aspects, the impedance measurement may be used by EI uterine pacemaker 100 to adjust the electrical energy output at electrodes 114A-114D. For example, as the impedance of the cervix decreases due to increased hydration, the amount of electrical energy that must be applied to control the uterus may also decrease. In some aspects, for example, the impedance may have a measured value between 2 and 65 ohm·meter (Ω·m) depending on the gestational age and stage of labor. As labor progresses, the impedance of the cervix decreases, for example, because the cervix becomes more hydrated or "ripens". In some aspects, an initial impedance value of the cervix may be measured upon insertion of the EI uterine pacemaker and the decrease in impedance as labor progresses may be monitored. For example, in some aspects, the electrical energy output at electrodes 114A-114D may be adjusted proportionately to the decrease in measured impedance.

The use of impedance to determine cervical ripeness for labor provides a significant improvement over current evaluation techniques which often rely on subjective evaluations made by a physician to determine whether labor can be induced by medical means. The use of impedance allows for a measurement based analysis and determinations of cervical ripeness for labor.

Figure 7:
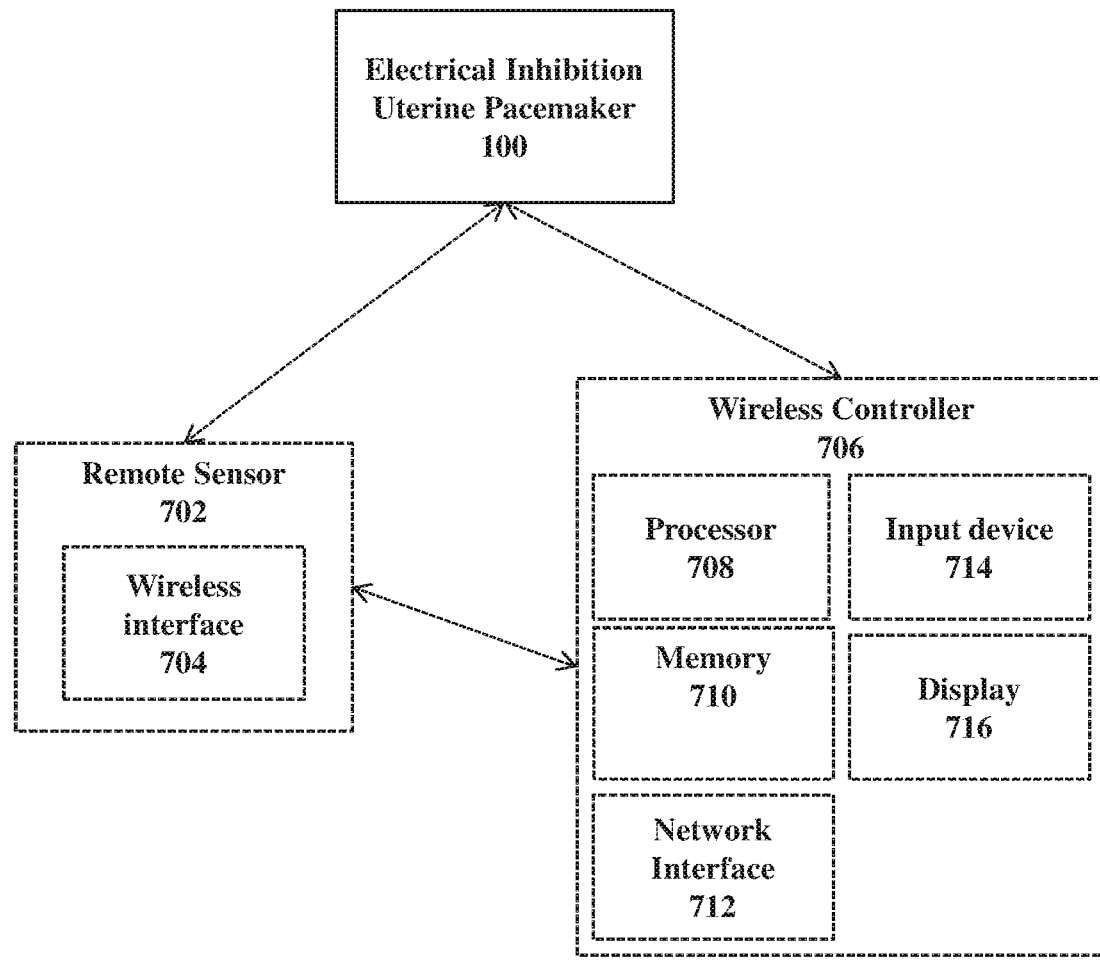
FIG. 7 is a system diagram illustrating a system employing the EI uterine pacemaker of FIG. 1A or 1B in accordance with an aspect of the present disclosure.

With reference now to FIG. 7, a system 700 for controlling uterine labor is disclosed. System 700 includes EI uterine pacemaker 100 as described above. In some aspects, EI uterine pacemaker 100 may be a stand-alone device that is pre-configured to control uterine labor using one or more of electrodes 114A-114D.

In some aspects, system 700 may include a remote sensor 702 that may wirelessly communicate with EI uterine pacemaker 100. For example, remote sensor 702 may be a sensor placed or positioned on an exterior surface of the patient's body, e.g., on the skin of the patient's chest, abdomen, etc. and may be used to sense electrical signals associated with contractions and/or fetal heart rate. As an example, remote sensor 702 may be a transducer that is attached to a patient's abdomen and configured to monitor the patient for electrical signals associated with contractions. In some aspects, for example, the remote sensor 702 may include a FDA approved abdominal uterine electromyography (EMG) or electrohysterography (EHG) monitors including, e.g. OBMedical™ LV1000, Monica Healthcare® AN24, OBTools™ TrueLabor™, Reproductive Research Technologies SureCall®, or other similar sensors. In some aspects, the remote sensor 702 may wirelessly transmit any monitored electrical signals to EI uterine pacemaker 100 using a wireless interface 704.

Wireless interface 704 may utilize wireless technologies and communication protocols such as, for example, Bluetooth®, WIFI (e.g., 802.11a/b/g/n), cellular networks (e.g., CDMA, GSM, M2M, and 3G/4G/4G LTE), near-field communications systems, satellite communications, or any other form of communication that allows remote sensor 702 to transmit or receive information. In some aspects wireless interface 704 may communicate with EI uterine pacemaker 100 via an intermediary network, for example, a local area network (LAN), wide area network (WAN), the internet, or other similar networks.

EI uterine pacemaker 100 may receive the electrical signal from sensor 702, e.g., at one or more of wireless receivers 316, 420, 520, 540, 620, and 640, depending on the configuration, and may activate, disable, or adjust the supply of electrical energy to electrodes 114A-114D based on the received electrical signal. For example, an electrical signal is detected from the patient by sensor 702 that indicates a contraction is occurring or will imminently occur, the electrical signal may be transmitted to EI uterine electrode 100 and EI uterine pacemaker 100 may apply electrical energy from some or all of electrodes 114A-114D to the patient's cervix counteract or enhance the contraction. In some aspects, the settings or configuration of the components of EI uterine pacemaker may be adjusted based on the electrical signal received from the sensor 702. For example, any of the frequency, pulse width, amplitude, or other similar parameters of the electrical energy output by EI uterine pacemaker 100 may be adjusted. In some aspects, the frequency may be fixed, for example, at 10 Hz, and the pulse width may be varied to provide the most effective duty cycle (ratio of EI on time when the current flows and the off time relative to the total pulse cycle or Hz). For example, the pulse width may be varied by about 20%. In some aspects, the amplitude, mA, may be variable and titrated for each patient.

In some aspects, system 700 may include a wireless controller 706. Wireless controller 706 includes a processor 708, memory 710, and a network interface 712. In some aspects, wireless controller 706 may also include an input device 714. In some aspects, wireless controller 706 may include a display 716. Non-limiting examples of wireless controllers 706 may include personal computers, laptops, tablets, smart devices including smart phones, smart wearable devices, smart watches, smart glasses, consoles, kiosks, custom devices, hand-held devices, stationary devices, or any other devices that may be configured to control EI uterine pacemaker 100.

In some aspects, wireless controller 706 may be used by a patient, a physician, other medical personnel, or any other party that is associated with treatment of the patient. In some aspects, more than one party may have a wireless controller 706 or may access the same wireless controller 706. For example, the patient may have a first wireless controller 706 and the physician may have a second wireless controller 706 where each of the wireless controllers may wirelessly control EI uterine pacemaker 100.

In some aspects, for example, the wireless controller 706 used by the patient may include limited functionality, e.g., allowing the patient to stop function of the pacemaker but not adjust the frequency or power output by the electrodes. In some aspects, for example, the wireless controller 706 used by the physician may have increase functionality and control as compared to the wireless controller 706 used by the patient, e.g., the capability to manipulate all of the settings of the EI uterine pacemaker. In some aspects, even the wireless controller 706 used by the physician may have limited functionality where, for example, the available functionality must comply with government guidelines.

In some aspects, the wireless controller 706 may require the receipt of log-in credentials that must be authenticated before providing additional functionality. For example, the physician or patient may log-in to the wireless controller 706 using personal authentication credentials before gaining access any functionality. In some aspects, the authentication of the credentials may determine the amount of functionality that is provided. For example, where no authentication credentials are provided, the functionality may be limited to a minimal set of functionality, for example, the capability to power off the EI uterine pacemaker 100 in the case of an emergency, view data regarding the settings of the EI uterine pacemaker, or other similar functionality that does not alter the operational parameters of the EI uterine pacemaker, e.g., frequency, voltage, etc. Depending on the authentication credentials used, additional functionality may be provided or "unlocked". For example, the patient may have a basic set of functionality that provides data on the function of the EI uterine pacemaker 100 while the physician may have an enhanced set of functionality that allows for the manipulation or adjustment of operating parameters of the EI uterine pacemaker 100.

Processor 708 may include, for example, a microcontroller, Field Programmable Gate Array (FPGA), or any other processor that is configured to perform various operations. Processor 708 may be configured to execute instructions as described below. These instructions may be stored, for example, in memory 710.

Memory 710 may include, for example, non-transitory computer readable media in the form of volatile memory, such as random access memory (RAM) and/or cache memory or others. Memory 710 may include, for example, other removable/non-removable, volatile/non-volatile storage media. By way of non-limiting examples only, memory 710 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 712 is configured to transmit and receive data or information to and from EI uterine electrode 100 or sensor 702 via wired or wireless connections. For example, network interface 712 may utilize wireless technologies and communication protocols such as Bluetooth®, WIFI (e.g., 802.11a/b/g/n), cellular networks (e.g., CDMA, GSM, M2M, and 3G/4G/4G LTE), near-field communications systems, satellite communications, or any other form of communication that allows wireless controller 706 to transmit or receive information. Network interface 712 may allow wireless controller 706 to communicate directly with one or more of EI uterine pacemaker 100 and sensor 702. In some aspects, network interface 712 may communicate with EI uterine pacemaker 100 or sensor 702 via an intermediary network, for example, a local area network (LAN), wide area network (WAN), the internet, or other similar networks.

Input device 714 may include, for example, a keyboard, a mouse, a touch-sensitive display, a keypad, a microphone, knobs, dials, buttons, or other similar input devices or any other input devices that may be used alone or together to provide a user with the capability to interact with wireless controller 706.

Display 716 may include, for example, a computer monitor, television, smart television, a display screen integrated into a personal computing device such as, for example, laptops, smart phones, smart watches, virtual reality headsets, smart wearable devices, or any other mechanism for displaying information to a user. In some aspects, display 716 may include a liquid crystal display (LCD), an e-paper/e-ink display, an organic LED (OLED) display, or other similar display technologies. In some aspects, display 716 may be touch-sensitive and may also function as an input device 714.

Wireless controller 706 is configured to allow a physician or other user to control EI uterine pacemaker 100 remotely. For example, wireless controller 706 may wirelessly receive signals or other data from EI uterine pacemaker 100 via network interface 712 and may wirelessly transmit signals or other data to EI uterine pacemaker 100 via network interface 712. Network interface 712 may communicate with any of wireless receivers 316, 420, 520, 540, 620, and 640, depending on the configuration.

In some aspects, for example, wireless controller 706 may transmit commands or otherwise control the output of EI uterine device 100. For example, a physician may utilize wireless controller 706 to modulate or adjust the settings of any of the timer frequency modulators, timer pulse width modulators, driver amplitude modulators, voltage to current sources, power boosts, and wireless receivers described above with respect to configurations 300-600. In some aspects, for example, the physician may modulate the frequency of the electrical signal output by the timer frequency modulator between 1 Hz and 100 Hz, the pulse width of the electrical signal output by the timer pulse width modulator between 1 ms and 120 ms, the amplitude of the electrical signal output by the driver amplitude modulator between 1 mA and 20 mA, and other similar settings, using wireless controller 706. In some aspects, the physician may control the polarity of the output of the electrical energy to the electrodes of EI uterine pacemaker 100 using wireless controller 706. In some aspects, the physician may also turn EI uterine pacemaker 100 "on" or "off" using wireless controller 706. For example, when the physician determines that labor may proceed, EI uterine pacemaker 100 may be turned off using wireless controller 706 to allow natural contractions to occur.

Figure 8:
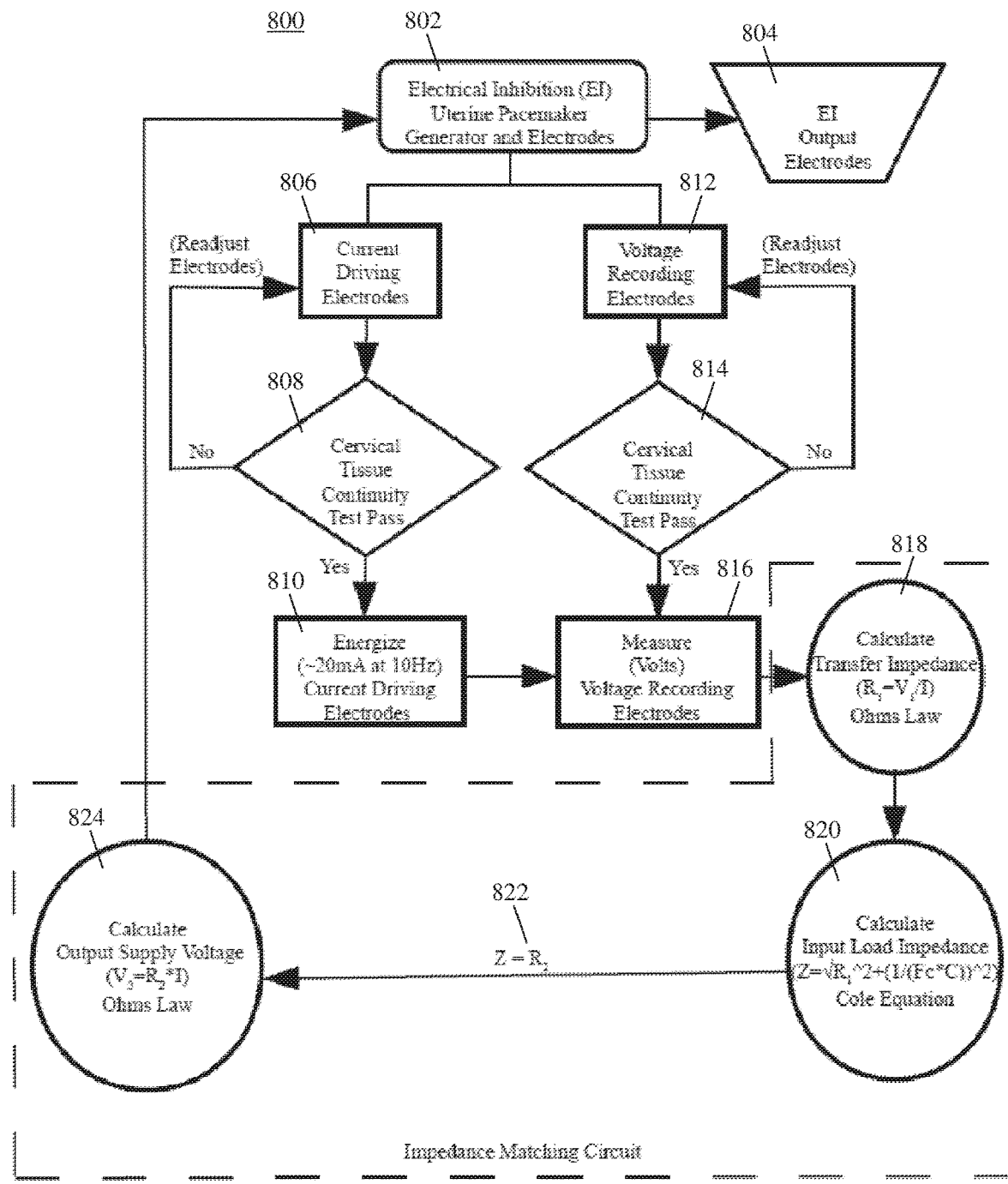
FIG. 8 is a flow chart of a method for controlling uterine contractions according to an embodiment of the present disclosure.

With reference now to FIG. 8, a method 800 for controlling uterine contractions is disclosed. At 802, EI uterine pacemaker 100 is activated to supply electrical energy to output electrodes 804, e.g., some or all of electrodes 114A-114D (FIGS. 1 and 2).

At 806, the current driving electrodes, e.g., a pair of electrodes 114A-114D (FIGS. 1 and 2), in some aspects, for example, electrodes 642A and 642B of configuration 600 (FIG. 6), may be initially activated at a low level current to test for cervical tissue continuity. For example, the low level current may be used to determine whether cervical tissue is disposed between the current driving electrodes and whether the current driving electrodes are in contact with the cervical tissue. For example, a small current may be applied between the active electrode and the passive electrode and if both electrodes are in contact with the tissue, the current will flow through the tissue and be measured as a resistance which may indicate a passed cervical tissue continuity test.

At 808, EI uterine pacemaker 100 determines whether the cervical tissue continuity test passes. If the continuity test does not pass, for example, if impedance between the electrodes is not below a predetermined threshold value, or no tissue resistance is detected between the electrodes, the current driving electrodes may be re-adjusted or repositioned at 806, for example, by the physician that inserted the EI uterine pacemaker 100 into the patient's vagina. If the continuity test passes, e.g., impedance between the current driving electrodes is below the pre-determined threshold value, the continuity test may pass and the current driving electrodes may be energized at 810. For example, the current driving electrodes may be energized to about 20 mA at about 10 Hz.

At 812, voltage recording electrodes, e.g., a pair of electrodes 114A-114D (FIGS. 1 and 2), in some aspects, for example, electrodes 622A and 622B of FIG. 6, may apply a low level current to cervical tissue to determine whether the cervical tissue passes a continuity test, e.g., whether there is cervical tissue disposed between the voltage recording electrodes and whether the voltage recording electrodes are in contact with the cervical tissue.

At 814, EI uterine pacemaker 100 determines whether the cervical tissue continuity test passes as described above. If the continuity test does not pass, for example, if impedance between the electrodes is not below a predetermined threshold value, the voltage recording electrodes may be re-adjusted as described above at 812. If the continuity test passes, e.g., impedance between the electrodes is below the pre-determined threshold value, the continuity test may pass and the voltage recording electrodes may be energized at 816 to continue measuring an impedance of the cervical tissue. In some aspects, the current driving electrodes and the voltage recording electrodes may be the same electrodes. For example, the current driving electrodes may be configured to sense an impedance of the cervical tissue by applying a low level current to the cervical tissue in between active applications of electrical energy to control the patient's uterine contractions. In some aspects, for example, the current driving electrodes may sense the impedance during the active application of electrical energy.

When both the current driving electrodes and the voltage recording electrodes have passed the cervical tissue continuity test and are activated, EI uterine pacemaker 100 may in some aspects perform impedance matching starting at 818.

At 818, EI uterine pacemaker 100 calculates a transfer impedance $R_1$ of the cervical tissue based on Ohms Law ($R_1=V_1/I$) where $V_1$ is voltage, I is current, and $R_1$ is measured at the passive voltage measuring electrode based on the formula. For example, the transfer impedance $R_1$ may be measured based on a voltage drop generated between the active electrode surface tissue load interface and the passive electrode tissue load interface. In some aspects, for example, as the tissue load resistance decreases, the voltage drop also decreases and the transfer impedance will decrease. Similar to the tissue impedance mentioned above, cervical tissue resistance (transfer impedance) in humans may vary widely depending on the stage of labor. In some aspects, the resistivity values may be between, for example, about 100 to about 300 ohm·cm.

At 820, EI uterine pacemaker 100 calculates impedance Z of the cervical tissue according to Cole's equation $$Z = \sqrt{\left(R_1^2 + \left(\frac{1}{F_c \times C}\right)^2\right)}$$

where Z is impedance, $R_1$ is transfer impedance calculated at 818, Fc is the characteristic frequency of cervical tissue, for example, based on a look-up table or predefined by a physician, and C is capacitance of the muscle cells. In some aspects, for example, C may be inversely proportional to Fc. For example, the muscle cell membranes include lipid bilayers that may function as a capacitor. The lipid bilayers control the exchange of electrically charged ions across the cell membrane and therefore the electrical potential of its interior relative to the exterior. For example, there may be two conductors (the inside and the outside of the cell), separated by an insulator (the membrane). This makes it possible to have different amounts of electrical charges inside and outside the cell i.e. the electrical equivalent of a capacitor.

At 822, EI uterine pacemaker 100 sets the input load impedance $R_2$ to the calculated impedance value Z.

At 824, EI uterine pacemaker 100 calculates output supply voltage $V_2$ using Ohms Law ($V_2=R_2*I$). Where the output supply voltage $V_2$ is equal to the input load impedance $R_2$ multiplied by the current I. The output supply voltage $V_2$ is then used to adjust the electrical energy output by EI uterine pacemaker 100 at 802 for example by changing the internal resistance of the EI uterine pacemaker 100 to output impedance that matches the cervical tissue load impedance.

In some aspects, for example, a decrease in the measured impedance of the cervical tissue may indicate an increase in the cervical ripeness and a progression of labor. In some aspects, the measured impedance value may be used to determine a likelihood of success of the EI treatment. For example, as the impedance value decreases, the likelihood of success of the EI treatment may also increase due to the progression of the patient's labor. For example, a decrease in the measured impedance indicates the uterine tissue has less resistance and therefore is more electrically active and contracting. With low resistance the natural preterm uterine electrical activity is able to travel throughout the whole uterus driving each contraction. This gives the EI uterine pacemaker 100 an increased chance of "capturing" or controlling the uterine muscle and inhibiting the preterm electrical activity and the preterm uterine mechanical contraction activity.

In some aspects, the measured impedance may also be transmitted to wireless controller 706 and presented to a physician or other user on display 716 for consideration by the physician or other user. For example, based on the measured impedance value, the physician may determine that the patient is likely to response well to the induction of labor.

In some aspects, EI uterine pacemaker 100 may be utilized to enhance contractions of the uterus. For example, where the patient's uterine contractions are not progressing toward labor, EI uterine pacemaker 100 may be configured to apply electrical to enhance the uterine contractions. For example, upon receipt of an indication that a uterine contraction is imminent, e.g., from sensor 702, EI uterine pacemaker 100 may apply electrical energy to the patient's cervix in a manner to facilitate and support the contraction. In some aspects, for example, the pulse width of the applied electrical energy may be adjusted to either inhibit contractions (e.g., a long pulse width) or enhance contractions (e.g., a short pulse width). In some aspects, the timing of the application of electrical energy may also be adjusted to enhance or inhibit the contractions. For example, a duty cycle greater than 10%, e.g., a long pulse width in the range of milliseconds, may be used to relax the cervix and inhibit contractions in the uterus while a duty cycle smaller than 1%, e.g., a short pulse width in the range of microseconds, may be used to stimulate contractions in the uterus.

In some aspects, after delivery of the baby, the contractions of the uterus still occur to push out the placenta. In some cases, however, the placenta may not detach from the uterus in a timely manner and the cervix may close before it can be removed. EI uterine pacemaker 100 may be utilized to relax the cervix through the controlled application of electrical energy to the cervix. For example, the EI uterine pacemaker 100 may be removed from the vagina before and during delivery of the baby and another EI uterine pacemaker 100 may be inserted into the vagina after delivery of the baby if necessary to control the cervix until the placenta is ready to be removed. The newly inserted EI uterine pacemaker 100 may apply electrical energy as described above to the cervix to relax the cervix, uterus, or both and maintain the cervix in a dilated state until the placenta is ready to be removed. For example, EI uterine pacemaker 100 may be used to inhibit uterine contractions associated with acute emergencies such as placental abruption, placental rupture, retained placenta, and Bandl's ring to provide physicians with additional time to treat these conditions. The newly inserted EI uterine pacemaker 100 may then be removed to allow the placenta to pass through the cervix and out of the vagina.

In some aspects, the EI uterine pacemaker 100 may apply energy to the patient's cervix in response to an impending uterine contraction as sensed by remote sensor 702. For example, remote sensor 702 may sense electrical activity in the patient's uterus that indicates an impending contraction and may transmit an indication of an impending transaction (or the sensed electrical activity) to EI uterine pacemaker 100. The EI uterine pacemaker 100 may then apply electrical energy to the cervix of the patient to inhibit the contraction. For example, the EI uterine pacemaker 100 may apply the electrical energy to the patient's cervix prior to the contraction to control the smooth muscle of the patient's uterus such that when the electrical energy generated by the patient that drives the contraction reaches the controlled smooth muscle, the contraction is inhibited. In some aspects, the electrical energy may be applied, for example, at about 10 Hz, for about 20 ms, at about 0-10 mA.

In some aspects, the EI uterine pacemaker 100 may apply energy to the patient's cervix in response to a failure of the patient's uterus to contract after pregnancy, also known as uterine atony. This may be common, for example, in cases where the pregnant uterus is overstretched, e.g., multiple pregnancy. A failure of the uterus to contract after pregnancy may present a dangerous situation for the patient. For example, bleeding of the uterine vessels is typically stopped once the myometrial fibers have contracted. Absent such contraction, however, it may become difficult or impossible to stop the bleeding without removing the post-partum uterus itself. The EI uterine pacemaker 100 may be used as described above to apply energy to the patient's cervix (and therefore to the uterus) to stimulate the myometrium to cause uterine contractions.

In some aspects, the EI uterine pacemaker 100 may apply energy to the patient's cervix in response to non-labor contractions, sometimes referred to as Braxton-Hicks contractions. Braxton-Hicks contractions occur during most, if not all, pregnancies. These contractions appear to arise from multiple foci in the myometrium and do not lead to changes in the cervix or productive labor. Instead, Braxton-Hicks contractions are perceived as painful cramping in the uterus and its supporting ligaments. These contractions are debilitating, can often be excruciating for a patient, often resulting in lost work hours. The EI uterine pacemaker 100 may be used as described above to apply energy to the patient's cervix (and therefore to the uterus) to inhibit pre-mature labor and Braxton-Hicks contractions.

In some aspects, the EI uterine pacemaker 100 may apply energy to the patient's cervix in response to uterine pain, e.g., cramps, pain, etc., experienced by the patient at the end of the menstrual cycle or during menstruation including pain due to dysmenorrhea. This cramping or pain may often be caused by myometrial contractions triggered by the production of prostaglandins by the myometrium. The EI uterine pacemaker 100 may be used as described above to apply energy to the patient's cervix (and therefore to the uterus) to inhibit these myometrial contractions and thereby reduce the associated cramping and pain experienced by the patient.

Figure 9:
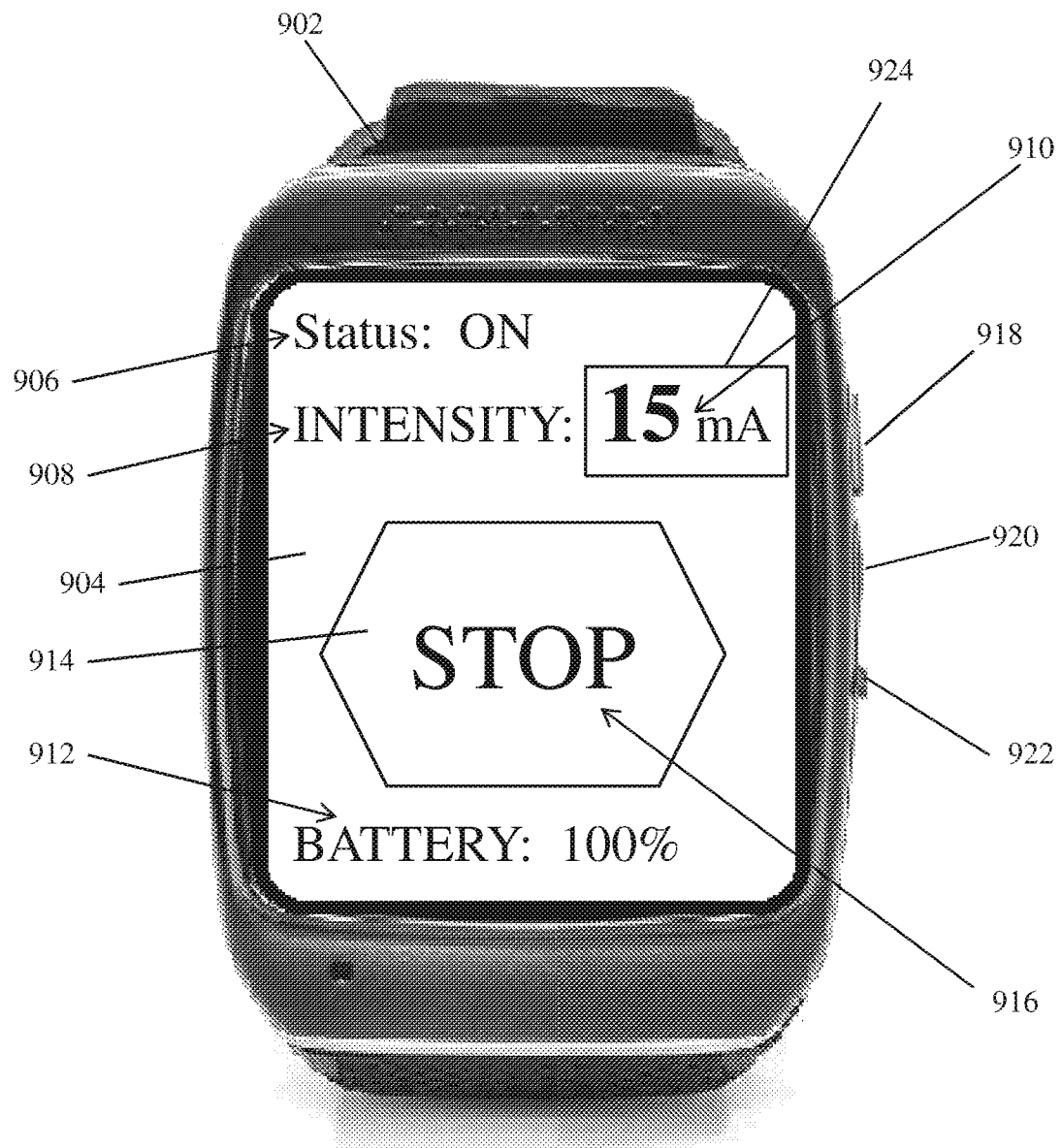
FIG. 9 is an illustration of an example wireless controller for use with the EI uterine pacemaker of FIG. 1A or 1B in accordance with an embodiment of the present disclosure.

In an aspect, with reference now to FIG. 9, an example wireless controller 706 is illustrated as wireless controller 902. Wireless controller 902 may include any of the features described above with respect to wireless controller 706. In some aspects, wireless controller 902 may include a smart watch worn on an exterior surface of the patient's body, e.g., the patient's wrist, and may be used to sense electrical signals associated with EI uterine pacemaker 100. As an example, wireless controller 902 may be a smart watch worn by the patient and configured to monitor and give the patient limited control of the EI uterine pacemaker 100.

In some aspects, wireless controller 902 includes a display 904 that is configured to present information to the patient or other user. In some aspects display 904 may be touch sensitive and useable as an input device 714. Display 904 may include any of the features described above with respect to display 716.

In some aspects, for example, display 904 may present a graphical user interface to a user including data associated with EI uterine pacemaker 100. For example, display 904 may present an indication of the status 906 of the EI uterine pacemaker 100 (e.g., on, off or any other status), a current intensity level 908 of the EI uterine pacemaker 100 (e.g., an intensity level 910 of 15 mA, and a battery status 912 of the EI uterine pacemaker 100. Any other data associated with EI uterine pacemaker 100 may also be presented on display 904 using the graphical user interface.

In some aspects, display 904 may also present an element 914 that is activatable by the patient or other user to stop or interrupt EI uterine pacemaker 100 from functioning. For example, display 904 may present a stop button 916 that may be activated or actuatable by the user to temporarily or permanently stop EI uterine pacemaker from functioning. In some aspects, if a patient has activated stop button 916 to stop EI uterine pacemaker 100 from functioning, EI uterine pacemaker 100 may only be restarted by a physician.

In some aspects, wireless controller 902 may include one or more elements that are activatable by a user to adjust settings associated with EI uterine pacemaker 100. For example, wireless controller 902 may include an increase intensity element 918 that may be activated or actuated by a user to increase the intensity of the EI uterine pacemaker 100, a decrease intensity element 920 that may be activated or actuated to decrease the intensity of the EI uterine pacemaker 100 and a set intensity element 922 that may be activated or actuated to lock in the increase or decrease.

In some aspects, the wireless controller 902 may transmit and receive electrical signals to and from EI uterine pacemaker 100 using network interface 712 (FIG. 7) as described above with reference to wireless controller 706. For example, when wireless controller 902 detects or receives an electrical signal from the EI uterine pacemaker 100 that indicates on/off status of the EI uterine pacemaker 906, display 904 may present the received status as status 906, the received current intensity setting as intensity setting 908, and the current battery level as battery status 912. In some aspects, the presented amplitude, mA, of the intensity level 910 may be variable and titrated by each patient with intensity controls 918, 920, and 922 to increase, decrease, and set the current intensity 910.

In some aspects, display 904 may present an intensity verification element 924, e.g., the box or the current intensity 910 value itself, which may provide an indication of whether wireless controller 902 is connected to EI uterine pacemaker 100. For example, the box around current intensity 910 or the current intensity 910 itself may flash (or not flash) to show that the wireless controller 902 is not connected to EI uterine pacemaker 100 and when a connection is established the flashing may stop (or flashing may start) to show that it is connected.

Figure 10:
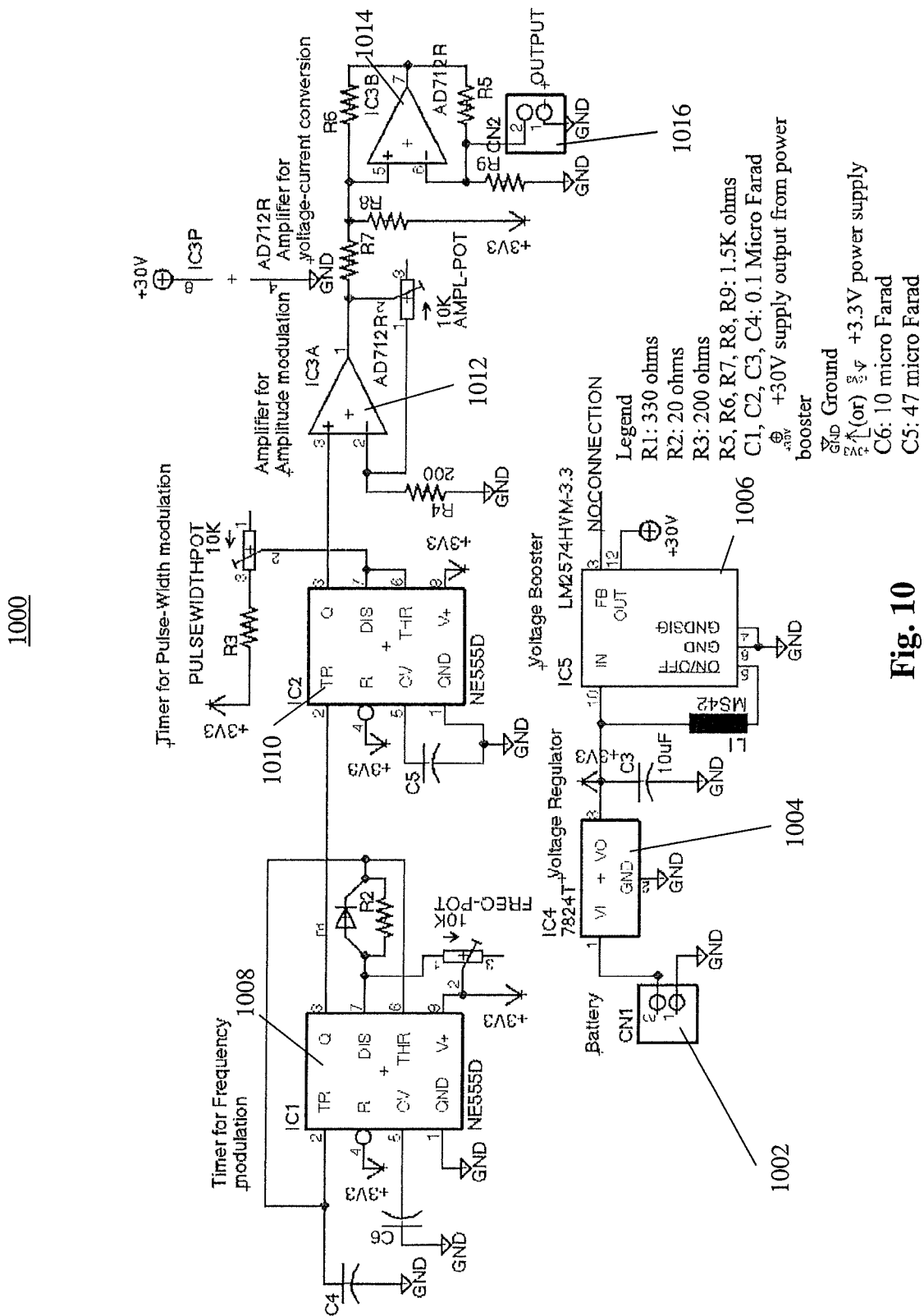
FIG. 10 is an electrical diagram of the EI uterine pacemaker of FIG. 1A or 1B according to an embodiment of the present disclosure.

With reference now to FIG. 10, an example circuit diagram 1000 for implementing any of configurations 300-600 is illustrated. Circuit diagram 1000 includes a power supply 1002, voltage regulator 1004, power booster 1006, timer frequency modulator 1008, timer pulse-width modulator 1010, driver amplitude modulator 1012, voltage-current source 1014, and output 1016.

Power supply 1002 is configured to provide battery power to EI uterine pacemaker 100 as described above with respect to power supplies 302, 402, 502, and 602.

Voltage regulator 1004 regulates the output power from power supply 1002 and feeds the regulated output power into power booster 1006 and timer frequency modulator 1006.

Power booster 1006 performs the functions described above with respect to power boosters 312, 414, 514, 534, 614, and 634.

Timer frequency modulator 1008 performs the functions described above with respect to timer frequency modulators 306, 406, 506, 526, 606, and 626.

Timer pulse-width modulator 1010 performs the functions described above with respect to timer pulse-width modulators 308, 408, 410, 508, 510, 528, 530, 608, 610, 628, and 630.

Driver amplitude modulator performs the functions described above with respect to driver amplitude modulators 310, 412, 512, 532, 612, and 632.

Voltage-current source 1014 performs the functions described above with respect to voltage-current sources 314, 416, 418, 516, 518, 536, 538, 616, 618, 636, and 638.

Output 1016 performs the functions described above with respect to electrodes 318A, 318B, 422A, 422B, 522A, 522B, 542A, 542B, 622A, 622B, 642A, and 642B.

With reference now to FIGS. 11-17, results generated when testing the EI uterine pacemaker 100 are presented.

Figure 11:
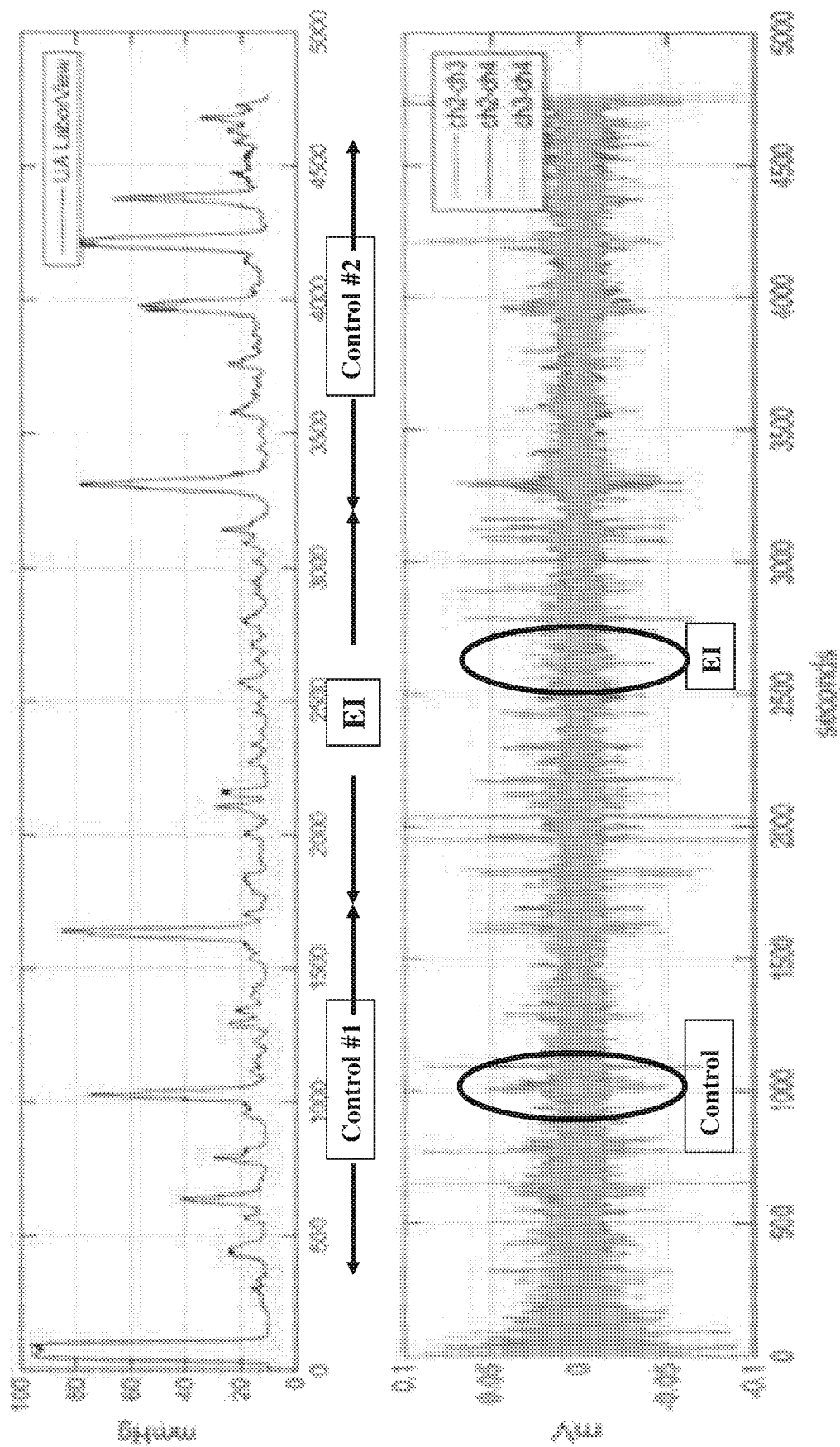
FIG. 11 is a chart showing the outputs of an EHG monitor (mmHg vs. seconds) and EMG monitor (mV vs. seconds) showing electrical activity exhibited by a patient's uterus during a first control cycle, activation of the EI uterine pacemaker, and a second control cycle.

As seen in FIG. 11, for example, the voltage (mV) and mmHg of electrical signals in the uterus were measured using EMG and EHG monitors. As can be seen in FIG. 11, during a first control cycle, the uterus exhibited a spike in electrical activity at the 1000 second mark. When the EI uterine pacemaker 100 was activated, however, a similar spike in electrical activity was not detected, e.g., at a 2500 second mark. When the EI uterine pacemaker 100 was deactivated, during a second control cycle, the uterus once again exhibited a spike in electrical activity, e.g., at the 4000 second mark. This shows that when the EI uterine pacemaker is active, electrical signals in the uterus are inhibited and the effects of a contraction are reduced or inhibited.

Figure 12A:
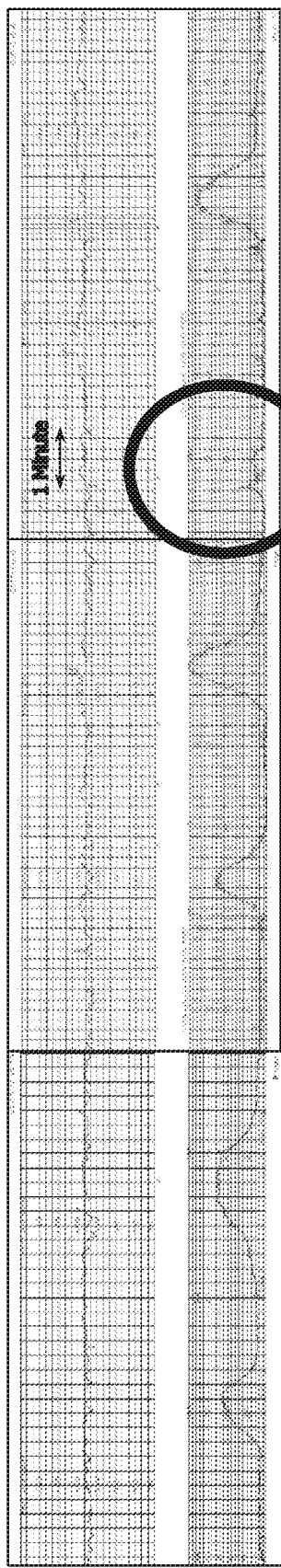
FIGS. 12A and 12B are charts showing the outputs of a tocodynamometric (TOCO) recording of uterine tension exhibited by a patient's uterus during control cycles and activation of the EI uterine pacemaker.
Figure 12B:
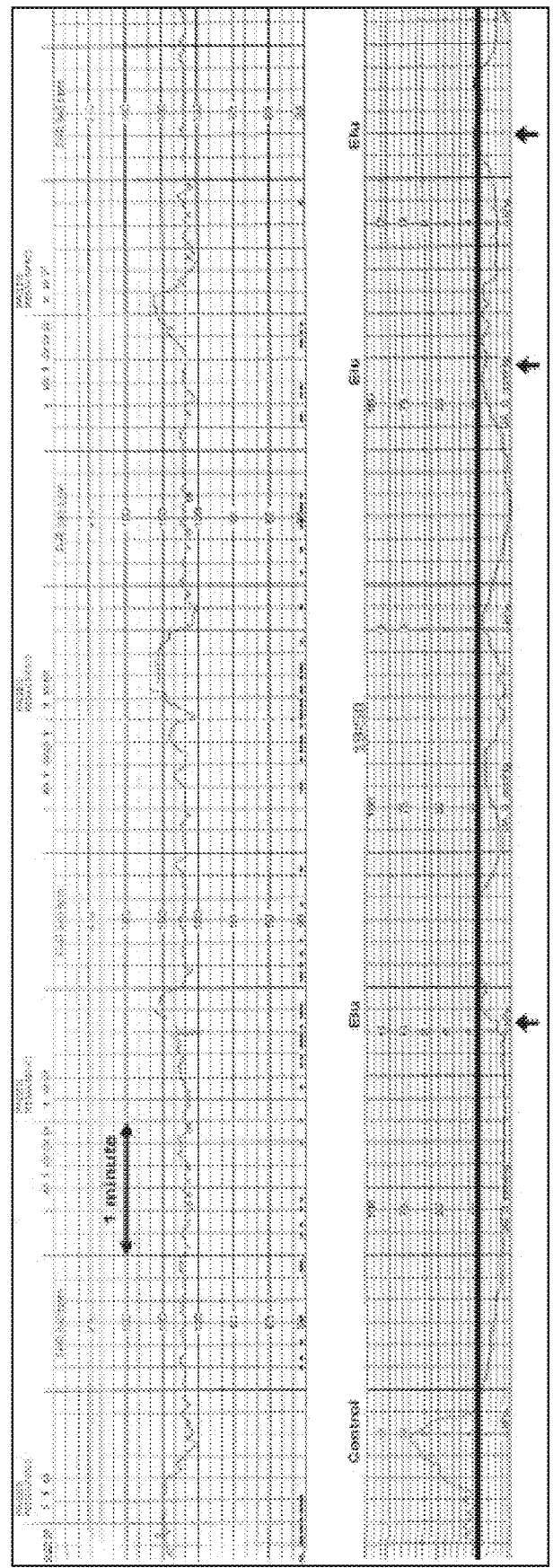

With reference now to the graphs shown in FIGS. 12A and 12B, a tocodynamometric (TOCO) recording was used to measure uterine tension during a number of control cycles and during activation of the EI uterine pacemaker 100. As can be seen in the graph of FIG. 12A, for example, during the control cycle leading up to the activation of the EI uterine pacemaker 100, the uterus exhibited periodic spikes in uterine tension, i.e. contractions. When the EI uterine pacemaker 100 was activated for 1 minute, however, a similar spike in uterine tension was not detected. When the EI uterine pacemaker 100 was deactivated, during a following control cycle, the uterus once again exhibited a spike in uterine tension. As seen in the top graph of FIG. 12B, for example, during a 1 minute interval when EI uterine pacemaker 100 is activated, uterine contractions are reduced or inhibited. As seen in the bottom graph of FIG. 12B, during a control cycle, the uterine tension spikes well above the thick black line which denotes approximately 25% tension. When EI uterine pacemaker 100 is active for 10 seconds, however, as denoted by each of the black arrows, the uterine tension for the remainder of the graph remains below the black line. Each of the graphs in FIGS. 12A and 12B show that when the EI uterine pacemaker is active, the spikes in uterine tension associated with contractions are inhibited.

Figure 13:
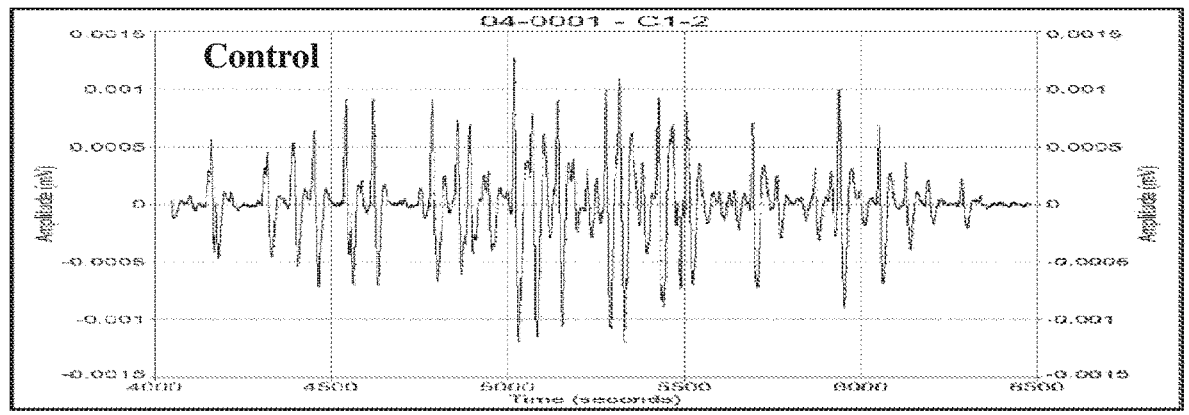
FIG. 13 is a chart showing the amplitude (mV) vs. time (s) of electrical activity exhibited by a patient's uterus during a control cycle.
Figure 14:
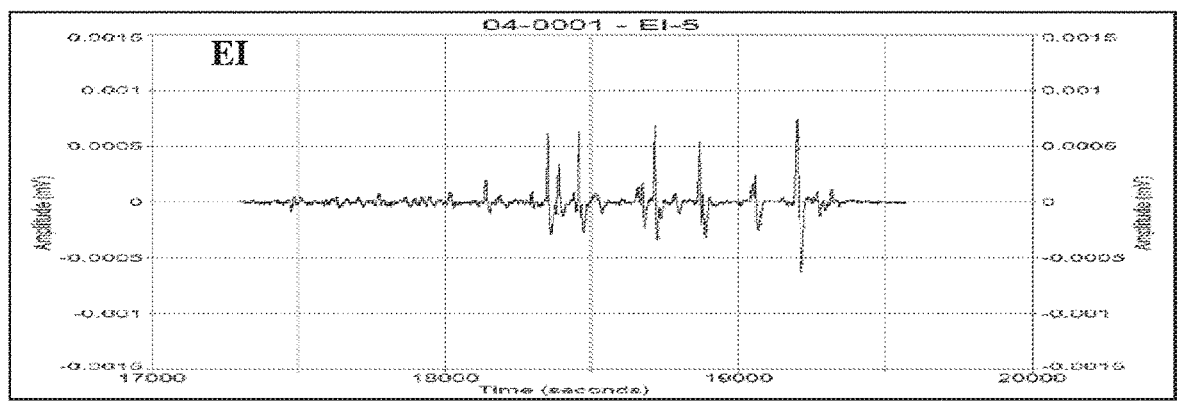
FIG. 14 is a chart showing the amplitude (mV) vs. time (s) of electrical activity exhibited by a patient's uterus during activation of the EI uterine pacemaker.

Referring now to FIGS. 13 and 14, a comparison of the amplitude of electrical activity in the uterus during a control cycle (FIG. 13) and activation of EI uterine pacemaker 100 (FIG. 14) are illustrated. As seen in FIG. 13, the amplitude of the electrical activity in the uterus due to contractions varied from approximately −0.0012 to approximately 0.0013. However, as seen in FIG. 14, when EI uterine pacemaker 100 is activated, the amplitude of the electrical activity in the uterus due to contractions is significantly reduced and varies from approximately −0.0006 to approximately 0.0007. This shows that when the EI uterine pacemaker is active, the amplitude of the electrical signals associated with contractions in the uterus are reduced or inhibited.

Figure 15:
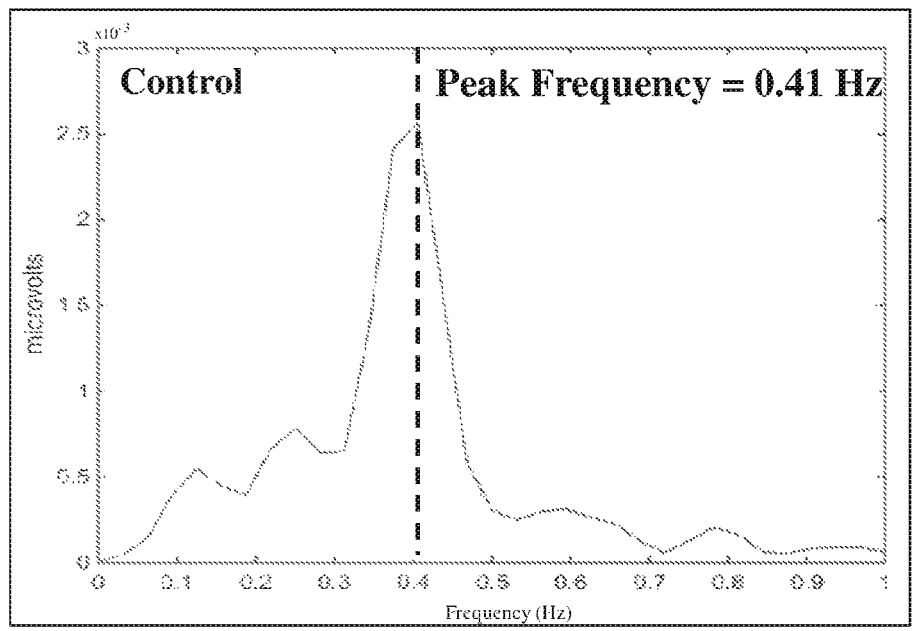
FIG. 15 is a chart showing the peak frequency (Hz) vs. voltage (mV) of the electrical activity exhibited by a patient's uterus during a control cycle.
Figure 16:
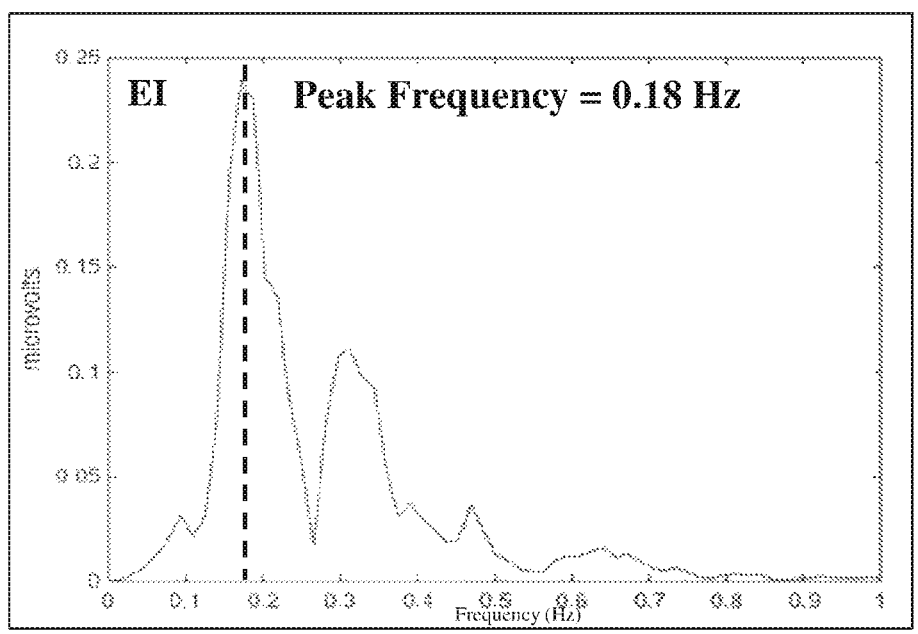
FIG. 16 is a chart showing the peak frequency (Hz) vs. voltage (mV) of the electrical activity exhibited by a patient's uterus during activation of the EI uterine pacemaker.

Referring now to FIGS. 15 and 16, a comparison of the peak frequency of electrical activity in the uterus during a control cycle (FIG. 15) and activation of EI uterine pacemaker 100 (FIG. 16) are illustrated. As seen in FIG. 15, the peak frequency of 0.41 Hz occurred at approximately 2.5 microvolts. However, as seen in FIG. 16, when EI uterine pacemaker 100 is activated, the peak frequency is reduced to 0.18 Hz at approximately 2.3 microvolts. This shows that when the EI uterine pacemaker is active, the peak frequency of the electrical signals associated with contractions in the uterus are reduced or inhibited.

Figure 17:
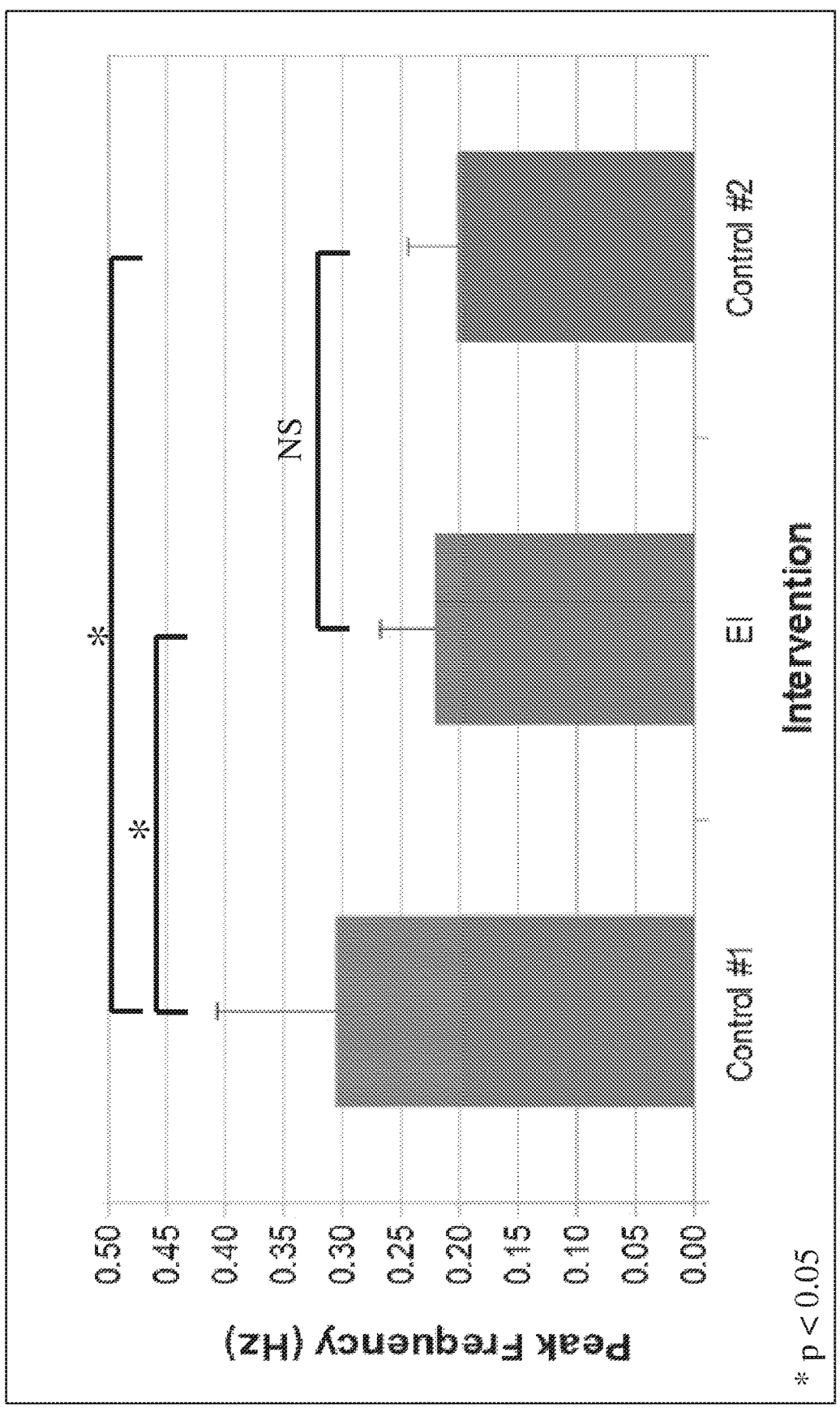
FIG. 17 is a bar chart illustrating the peak frequency (Hz) of electrical activity exhibited by a patient's uterus for each of a first control cycle, activation of the EI uterine pacemaker, and a second control cycle.

Referring now to FIG. 17, a comparison of the peak frequency of electrical activity in the uterus during a first control cycle, activation of EI uterine pacemaker 100, and a second control cycle following deactivation of the EI uterine pacemaker 100 are illustrated. For example, during the first control cycle, a peak frequency of approximately 0.30 Hz was detected. During activation of the EI uterine pacemaker 100, a peak frequency of approximately 0.22 was detected. During the second control cycle, a peak frequency of approximately 0.20 was detected. As shown in FIG. 17, the detected peak frequency in the first control cycle is statistically (p) different at the 0.05 level than the detected peak frequencies during activation of the EI uterine pacemaker 100 and the second control cycle while there is no statistically significant difference (NS) between the detected peak frequency during activation of the EI uterine pacemaker 100 and the second control cycle. This shows that the activation of EI uterine pacemaker 100 not only reduces the peak frequency as compared to the first control cycle, but that the effects of the EI uterine pacemaker 100 may last for a time after the EI uterine pacemaker 100 is deactivated, as seen from the low peak frequency exhibited during the second control cycle.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A wireless apparatus for controlling uterine contractions comprising:
   a housing configured to be fully inserted into and removable from the vagina of a patient adjacent to the cervix; and
   an energy generating device coupled to the housing, the energy generating device comprising:
   first and second electrodes configured to apply electrical energy to the cervix of the patient;
   a battery in electrical communication with the first and second electrodes;
   a wireless communication interface configured to wirelessly receive data from at least one sensor, the data comprising an indication that an electrical signal has been sensed by the at least one sensor from the uterus of the patient, the sensed electrical signal indicating that a contraction of the uterus is imminent;
   a generator circuit in electrical communication with the first and second electrodes and the battery and configured to cause the battery to supply electrical energy to the first and second electrodes, the first and second electrodes configured to apply the electrical energy to the uterus of the patient via the cervix of the patient to control contractions of the uterus in order to enhance or stimulate the contractions;
   an impedance matching circuit in electrical communication with the first and second electrodes, the impedance matching circuit configured to determine an impedance value of the cervix of the patient based on electrical energy applied to the cervix by the first and second electrodes;
   a controller in electrical communication with the wireless communication interface, the generator circuit, and the impedance matching circuit, the controller configured to:
   receive the data from the at least one sensor via the wireless communication interface;
   in response to receiving the data, cause the generator circuit to supply electrical energy to the first and second electrodes from the battery to control the uterus of the patient;
   receive the determined impedance value from the impedance matching circuit; and
   adjust the electrical energy supplied by the generator circuit to the first and second electrodes based on the determined impedance value.

2. The wireless apparatus of claim 1, the energy generating device further comprising at least a third electrode in electrical communication with the generator circuit, the generator circuit configured to cause the battery to supply electrical energy to the third electrode, the third electrode configured to apply the electrical energy to the cervix of the patient to control the cervix of the patient.

3. The wireless apparatus of claim 1, wherein the housing is configured to transition between a first state and at least a second state, the second state configured for insertion into the vagina of the patient.

4. The wireless apparatus of claim 3, wherein the housing is biased toward the first state.

5. The wireless apparatus of claim 1, wherein the generator circuit is configured to cause the battery to supply electrical energy to the first and second electrodes according to a waveform.

6. The wireless apparatus of claim 1, wherein the controller is configured to cause the generator circuit to supply the electrical energy to the first and second electrodes in a plurality of pulses.

7. The wireless apparatus of claim 6, wherein the controller is further configured to reverse a polarity of the electrical energy for at least one of the plurality of pulses.

8. The wireless apparatus of claim 1, wherein the controller is further configured to:
receive monitoring data from the at least one sensor, the monitoring data generated by the at least one sensor based at least in part on a sensed effect of the application of the electrical energy to the patient's uterus via the cervix; and
cause the generator circuit to adjust the supply of electrical energy to the first and second electrodes based on the monitoring data.

9. The wireless apparatus of claim 1, wherein the controller is further configured to:
determine that the received impedance value is below a pre-determined threshold value; and
in response to the determination that the received impedance value is below a pre-determined threshold value, cause the generator circuit to adjust the supply of electrical energy to the first and second electrodes, the adjustment to the supply of electrical energy configured to enhance the imminent contraction of the uterus.

10. The wireless apparatus of claim 1, wherein the controller is further configured to:
determine that the received impedance value is below a pre-determine threshold value; and
in response to the determination that the received impedance value is below a pre-determined threshold value, transmit an indication that the cervix is ripe for labor to a wireless controller associated with a physician.

11. A method of controlling uterine contractions of a patient comprising:
receiving, via a wireless communication interface of a wireless apparatus that is fully inserted into the patient's vagina adjacent to the cervix, data from at least one sensor, the data comprising an indication that an electrical signal has been sensed by the at least one sensor from the uterus of the patient, the sensed electrical signal indicating that a contraction of the uterus is imminent;
in response to receiving the data, causing, by a controller of the wireless apparatus, a generator circuit of the wireless apparatus to supply electrical energy from a battery of the wireless apparatus to an energy applicator of the wireless apparatus, the energy applicator of the wireless apparatus configured apply the supplied electrical energy to the uterus of the patient via the cervix of the patient to control contractions of the patient's uterus in order to enhance or stimulate the contractions.

12. The method of claim 11, wherein the energy applicator of the wireless apparatus comprises at least two electrodes in electrical communication with the generator circuit, the generator circuit configured to cause the battery to supply electrical energy to the at least two electrodes, the at least two electrodes configured to apply the electrical energy to the cervix of the patient to control the cervix of the patient.

13. The method of claim 11, wherein the generator circuit is configured to cause the battery to supply electrical energy to the energy applicator according to a waveform.

14. The method of claim 11, wherein the controller is configured to cause the generator circuit to supply the electrical energy to the energy applicator in a plurality of pulses.

15. The method of claim 14, wherein the controller is further configured to reverse a polarity of the electrical energy for at least one of the plurality of pulses.

16. The method of claim 11, further comprising:
receiving monitoring data from the at least one sensor, the monitoring data generated by the at least one sensor based at least in part on a sensed effect of the application of the electrical energy to the patient's uterus via the cervix; and
causing the generator circuit to adjust the supply of electrical energy to the energy applicator based on the monitoring data.

17. The method of claim 11, further comprising:
determining an impedance value of the cervix of the patient based on electrical energy applied to the cervix by the energy applicator;
determining that the impedance value is below a pre-determined threshold value; and
in response to the determination that the impedance value is below a pre-determined threshold value, causing the generator circuit to adjust the supply of electrical energy to the energy applicator, the adjustment to the supply of electrical energy configured to enhance the imminent contraction of the uterus.

18. The method of claim 11, further comprising:
determining an impedance value of the cervix of the patient based on electrical energy applied to the cervix by the energy applicator
determining that the impedance value is below a pre-determine threshold value; and
in response to the determination that the impedance value is below a pre-determined threshold value, transmitting an indication that the cervix is ripe for labor to a wireless controller associated with a physician.

19. A system comprising:
at least one sensor configured to monitor a patient's uterus and sense an electrical signal from the uterus, the sensed electrical signal indicating that a contraction of the uterus is imminent;
a wireless apparatus for controlling uterine contractions comprising:
a housing configured to be fully inserted into and removable from the vagina of a patient adjacent to the cervix; and
an energy generating device coupled to the housing, the energy generating device comprising:
an energy applicator configured to apply electrical energy to the cervix of the patient;
a battery in electrical communication with the energy applicator;
a wireless communication interface configured to wirelessly receive data from the at least one sensor, the data comprising an indication that an electrical signal has been sensed by the at least one sensor from the uterus of the patient, the sensed electrical signal indicating that a contraction of the uterus is imminent;

a generator circuit in electrical communication with a first and second electrodes and the battery and configured to cause the battery to supply electrical energy to the first and second electrodes, the first and second electrodes configured to apply the electrical energy to the uterus of the patient via the cervix of the patient to control contractions of the uterus in order to enhance or stimulate the contractions;

an impedance matching circuit in electrical communication with the first and second electrodes, the impedance matching circuit configured to determine an impedance value of the cervix of the patient based on electrical energy applied to the cervix by the first and second electrodes;

a controller in electrical communication with the wireless communication interface, the generator circuit, and the impedance matching circuit, the controller configured to:

receive the data from the at least one sensor via the wireless communication interface;

in response to receiving the data, cause the generator circuit to supply electrical energy to the first and second electrodes from the battery to control the uterus of the patient;

receive the determined impedance value from the impedance matching circuit; and adjust the electrical energy supplied by the generator circuit to the first and second electrodes based on the determined impedance value.

20. The system of claim 19, further comprising:

a computing device associated with a physician and configured to wirelessly communicate with the wireless apparatus, wherein the controller of the wireless apparatus is further configured to:

determine that the received impedance value is below a pre-determine threshold value; and in response to the determination that the received impedance value is below a pre-determined threshold value, transmit an indication that the cervix is ripe for labor to the computing device associated with a physician.

21. The system of claim 19, further comprising:

a wearable computing device associated with a patient and configured to wirelessly communicate with the wireless apparatus, wherein the wearable computing device is configured to:

receive data from the wireless apparatus;

determine, based on the received data, an on/off status of the wireless apparatus; and determine, based on the received data, a current intensity setting of the wireless apparatus;

determine, based on the received data, a battery level of the wireless apparatus;

present to the patient via a display of the wearable computing device the determined on/off status, current intensity setting, and battery level of the wireless apparatus;

receive from the patient an activation of at least one element of the wearable computing device, activation of the at least one element configured to adjust the current intensity setting by at least one of increasing, decreasing, or setting the current intensity setting; and based at least in part on the activation of the at least one element, transmit to the wireless apparatus a command to adjust the intensity of the electrical energy output by the wireless apparatus based on the adjusted current intensity setting.

22. The system of claim 19, further comprising:

a wearable computing device associated with a patient and configured to wirelessly communicate with the wireless apparatus, wherein the wearable computing device is configured to:

present to the patient via a display of the wearable computing device a stop element that, when activated is configured to stop the output of electrical energy by the wireless apparatus;

receive from the patient an activation of the stop element; and in response to receiving the activation of the stop element, transmit to the wireless apparatus a command to stop the output of the electrical energy.

* * * * *